(12) United States Patent
Yeatman et al.

(10) Patent No.: US 7,276,581 B2
(45) Date of Patent: Oct. 2, 2007

(54) MUTATED SRC ONCOGENE COMPOSITION AND METHODS

(75) Inventors: Timothy J. Yeatman, Tampa, FL (US); Rosalyn B. Irby, Tampa, FL (US)

(73) Assignee: University of South Florida, Tampa, FL (US)

( * ) Notice: Subject to any disclaimer, the term of this patent is extended or adjusted under 35 U.S.C. 154(b) by 399 days.

(21) Appl. No.: 10/887,588

(22) Filed: Jul. 9, 2004

(65) Prior Publication Data

US 2004/0261142 A1 Dec. 23, 2004

Related U.S. Application Data

(63) Continuation of application No. 09/444,711, filed on Nov. 24, 1999, now Pat. No. 6,764,833.

(51) Int. Cl.
| | |
|---|---|
| C07K 1/00 | (2006.01) |
| C07K 14/00 | (2006.01) |
| C07K 17/00 | (2006.01) |
| C07K 16/00 | (2006.01) |
| C07K 2/00 | (2006.01) |
| C07K 4/00 | (2006.01) |
| A61K 38/00 | (2006.01) |
| A01K 67/00 | (2006.01) |
| A01K 67/033 | (2006.01) |
| A01K 67/027 | (2006.01) |
| C12N 15/00 | (2006.01) |
| A61K 39/395 | (2006.01) |

(52) U.S. Cl. .................... 530/350; 530/300; 436/86; 424/9.1; 424/9.2; 424/184.1; 424/185.1; 514/1; 514/2; 514/4

(58) Field of Classification Search ............ 530/300, 530/350; 436/86; 424/9.1, 9.2, 184.1, 185.1; 514/1, 2, 4
See application file for complete search history.

(56) References Cited

U.S. PATENT DOCUMENTS 5,336,615 A 8/1994 Bell et al.

FOREIGN PATENT DOCUMENTS

WO    WO93/14193 A1    7/1993

OTHER PUBLICATIONS

Stehelin et al. "DNA related to the transforming gene(s) of avian sarcoma viruses is presenting normal avian DNA" Nature, 1976, 260:170-173.
Brugee et al. "Identification of a transformation-specific antigen induced by an avian sarcoma virus" Nature, 1977, 269:346-348.
Jove et al. "Cell transformation by the viral SRC oncogene" Annu. Rev. Cell Dev. Biol., 1987, 3:31-56.
Thomas et al. "Cellular functions regulated by SRC family kinases" Annu. Rev. of Cell Dev. Biol., 1997, 13:513-609.
Hamaguchi et al. "Augmentation of metalloproteinase (gelatinase) activity secreted from Rous sarcoma virus-infected cells correlates with transforming activity of src" Oncogene, 1995, 10:1037-1043.
Egan et al. "Transformation by oncogenes encoding protein kinases induces the metastatic phenotype" Science, 1987, 238:202-205.
Tatsuka et al. "Different metastatic potentials of ras- and src-transformed BALB/c 3T3 A31 variant cells" Mol. Carcinogenesis, 1996, 15:300-308.
Rosen et al. "Analysis of $pp60^{c-src}$ protein kinase activity in human tumor cell lines and tissues" J. Biol. Chem., 1986, 261:13754-13759.
Bolen et al. "Activation of $pp60^{c-src}$ protein kinase activity in human colon carcinoma" Proc. Natl. Acad. Sci. USA, 1987, 84:2251-2255.
Cartwright et al. "$pp60^{c-src}$ activation in human colon carcinoma" Amer. Soc. for Clinical Invest., Inc., 1989, 83:2025-2033.
Talamonti et al. "Increase in activity and level of $pp60^{c-src}$ in progressive stages of human colorectal cancer" J. Clin. Invest., 1991, 91:53-60.
Cartwright et al. "Elevated c-Src tyrosine kinase activity in premalignant epithelia of ulcerative colitis" J. Clin. Invest., 1994, 93:509-515.
Termuhlen et al. "Site-specific differences in $pp60^{c-src}$ activity in human colorectal metastases" J. Surg. Res., 1993, 54:293-298.
Mao et al. "Activation of c-Src by receptor tyrosine kinases in human colon cancer cells with high metastatic potential" Oncogene, 1997, 15:3083-3090.
Cooper et al. "$Tyr^{527}$ is phosphorylated in $pp60^{c-src}$: Implications for regulation" Science, 1986, 231:1432-1434.
Cartwright et al. "Cell transformation by $pp60^{c-src}$ mutated in the carboxy-terminal regulatory domain" Cell, 1987, 49:83-91.
Dmiecik et al. "Activation and suppression of $pp60^{c-src}$ transforming ability by mutation of its primary sites of tyrosine phosphorylation" Cell, 1987, 49:65-73.
Piwnica-Worms et al. "Tyrosine phosphorylation regulates the biochemical and biological properties of $pp60^{c-src}$" Cell, 1987, 49:75-82.
Reynolds et al. "Activation of the oncogenic potential of the avian cellular src protein by specific structural alteration of the carboxy terminus" Embo. J., 1987, 6:2359-2364.
Jove et al. "In vivo phosphorylation states and kinase activities of transforming $p60^{c-src}$ mutants" Oncogene Res., 1989, 5:49-60.

(Continued)

Primary Examiner—Alana M. Harris
(74) Attorney, Agent, or Firm—Saliwanchik, Lloyd & Saliwanchik

(57) ABSTRACT

The present invention provides a mutant oligonucleotide composition encoding a cellular c-Src tyrosine kinase oncogene. Methods for isolating, expressing and characterizing recombinant Src mutant polypeptide are also provided. The invention further relates to methods for utilizing such oligonucleotides, polypeptides, agonists and antagonists for applications, which relate to research, diagnostics, and clinical arts. More specifically, this invention provides methods of diagnosing, treating, immunizing, and creating transgenic animals based on use of such mutant Src.

3 Claims, 4 Drawing Sheets

OTHER PUBLICATIONS

Figure 1A:
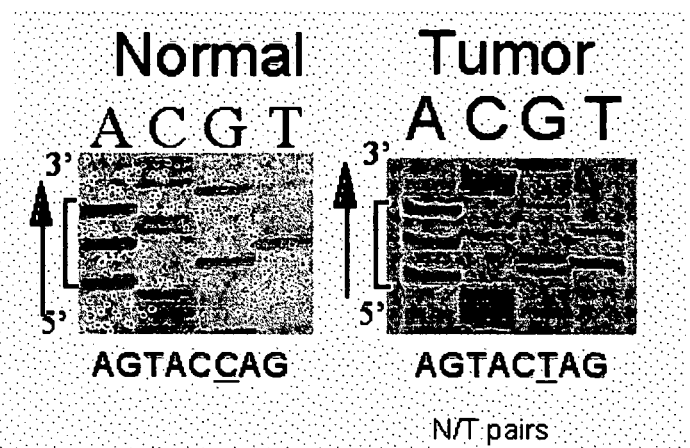

Bjorge et al. "Characterization of two activated mutants of human pp60$^{c-src}$ that escape c-Src kinase regulation by instinct mechanisms" *J. Biol. Chem.*, 1995, 270:24222-24228.

Wang et al. "c-src structure in human cancers with elevated pp60$^{c-src}$ activity" *Bre. J. Cancer*, 1991, 64:531-533.

Snyder et al. "Phosphorylation of tyrosine-416 is not required for the transforming properties and kinase activity of pp60$^{c-src}$" *Cell*, 1983, 32:891-901.

Tanaka et al. "DNA sequence encoding the amino-terminal region of the human c-*src* protein: Implications of sequence divergence among *src*-type kinase oncogenes" *Mol. Cell Biol.*, 1987, 7:1978-1983.

Tanaka et al. "Expression of a molecularly cloned human c-*src* oncogene by using a replication-competent retroviral vector" *Mol. Cell Biol.*, 1986, 6:3900-3909.

Mao et al. "Activation of c-Src by receptor tyrosine kinases in human colon cancer cells with high metastatic potential" *Oncogene*, 1997, 15:3083-3090.

Jove et al. "Enzymatically inactive p60$^{c-src}$ mutant with altered ATP-binding site is fully phosphorylated in its carboxy-terminal regulatory region" *Cell*, 1987, 50:937-943.

Nucleic acid database sheet. Data from U.S. Patent No. 5,336,615, 1994.

Amino acid and nucleic acid databases, Sequence 3 from U.S. Appl. No. 07/820,011, now U.S. Patent 5,336,615.

Nucleic acid database sheet, Accession No. AAQ46688, WO 93/14193A, Yale University, Jul. 22, 1993.

Nucleic acid/amino acid database sheet: Accession No. AAR39706, WO 93/14193A, Yale University, Jul. 22, 1993.

Nucleic acid database sheet, Sequence 3, U.S. Patent No. 5,336,615, Aug. 9, 1994.

Nucleic acid/amino acid database sheet, Sequence 4, U.S. Patent No. 5,336,615, Aug. 9, 1994.

Taurog et al. "HLA-B27 in inbred and non-inbred transgenic mice" *J. Immunology*, 1988, 141:4020-4023.

Houdebine "Production of pharmaceutical proteins from transgenic animals" *J. Biotechnology* 1994, 34:269-287.

Mullins and Mullins "Perspectives series: Molecular medicine in genetically engineered animals" *J. Clin. Invest.*, 1996, 98(11)supplement:S37-S40.

Mullins et al. "Expression of the DBA/2J Ren-2 gene in the adrenal gland of transgenic mice" *EMBO J.*, 1989, 8(13):4065-4072.

Mullins et al. "Fulminant hypertension in transgenic rats harbouring the mouse Ren-2 gene" *Nature*, 1990, 344:541-544.

Hammer et al. "Spontaneous inflammatory disease in transgenic rats expressing HLA-B27 and human B2m: an animal model of HLA-B27-associated human disorders" *Cell*, 1990, 63:1099-1112.

Mullins and Mullins "Transgenesis in nonmurine species" *Hypertension*, 1993, 22:630-633.

Overbeek, P.S. Transgenic Animal Technology, A laboratory handbook, Pinkert, C.A. Ed., Academic Press, 1$^{st}$ Edition, Jan. 15, 1994, pp. 96-98.

Wall, R.J. "Transgenic livestock: progress and prospects for the future" *Theriogenology*, 1996, 45:57-68.

Kappel et al "Regulating gene expression in transgenic animals" *Curr. Opinion Biotech.*, 1992, 3:548-553.

Stratagene 1997/1998 catalog, p. 118 and accompanying instruction manual.

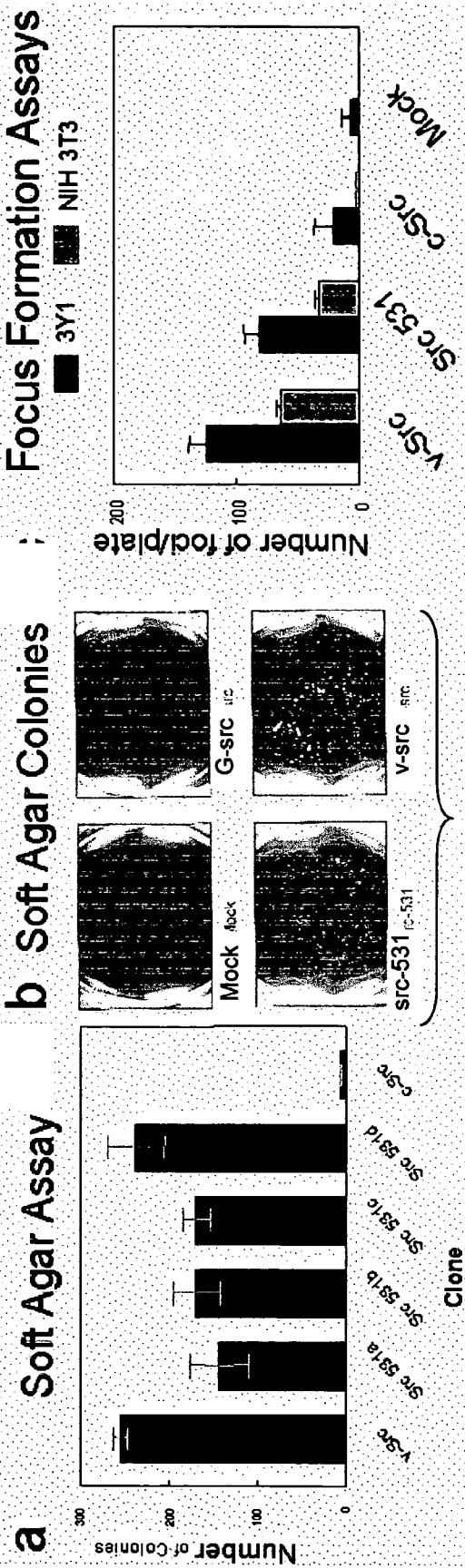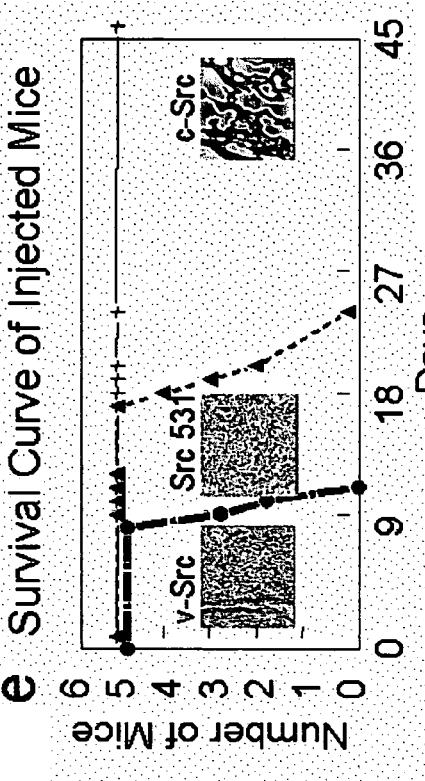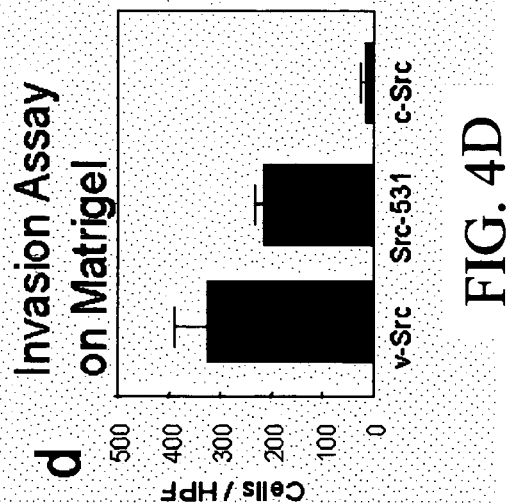
FIG. 4A
FIG. 4B
FIG. 4C
FIG. 4D
FIG. 4E

SEQUENCE LISTING

```
<160> NUMBER OF SEQ ID NOS: 7

<210> SEQ ID NO 1
<211> LENGTH: 1611
<212> TYPE: DNA
<213> ORGANISM: Homo sapiens
<220> FEATURE:
<221> NAME/KEY: misc_feature
<222> LOCATION: (1)..(1611)
<223> OTHER INFORMATION: nucleotide sequence of normal c-Src oncogene
      coding region
<220> FEATURE:
<221> NAME/KEY: CDS
<222> LOCATION: (1)..(1611)
<223> OTHER INFORMATION:

<400> SEQUENCE: 1 atg ggt agc aac aag agc aag ccc aag gat gcc agc cag cgg cgc cgc        48
Met Gly Ser Asn Lys Ser Lys Pro Lys Asp Ala Ser Gln Arg Arg Arg
1               5                   10                  15 agc ctg gag ccc gcc gag aac gtg cac ggc gct ggg ggc gct ttc            96
Ser Leu Glu Pro Ala Glu Asn Val His Gly Ala Gly Gly Ala Phe
                20                  25                  30 ccc gcc tcg cag acc ccc agc aag cca gcc tcg gcc gac ggc cac cgc       144
Pro Ala Ser Gln Thr Pro Ser Lys Pro Ala Ser Ala Asp Gly His Arg
            35                  40                  45 ggc ccc agc gcg gcc ttc gcc ccc gcg gcc gcc gag ccc aag ctg ttc       192
Gly Pro Ser Ala Ala Phe Ala Pro Ala Ala Ala Glu Pro Lys Leu Phe
        50                  55                  60 gga ggc ttc aac tcc tcg gac acc gtc acc tcc ccg cag agg gcg ggc       240
Gly Gly Phe Asn Ser Ser Asp Thr Val Thr Ser Pro Gln Arg Ala Gly
65                  70                  75                  80 ccg ctg gcc ggt gga gtg acc acc ttt gtg gcc ctc tat gac tat gag       288
Pro Leu Ala Gly Gly Val Thr Thr Phe Val Ala Leu Tyr Asp Tyr Glu
                85                  90                  95 tct agg acg gag aca gac ctg tcc ttc aag aaa ggc gag cgg ctc cag       336
Ser Arg Thr Glu Thr Asp Leu Ser Phe Lys Lys Gly Glu Arg Leu Gln
                100                 105                 110 att gtc aac aac acg gag gga gac tgg tgg ctg gcc cac tcg ctc agc       384
Ile Val Asn Asn Thr Glu Gly Asp Trp Trp Leu Ala His Ser Leu Ser
            115                 120                 125 aca gga cag aca ggc tac atc ccc agc aac tac gtg gcg ccc tcc gac       432
Thr Gly Gln Thr Gly Tyr Ile Pro Ser Asn Tyr Val Ala Pro Ser Asp
        130                 135                 140 tcc atc cag gct gag gag tgg tat ttt ggc aag atc acc aga cgg gag       480
Ser Ile Gln Ala Glu Glu Trp Tyr Phe Gly Lys Ile Thr Arg Arg Glu
145                 150                 155                 160 tca gag cgg tta ctg ctc aat gca gag aac ccg aga ggg acc ttc ctc       528
Ser Glu Arg Leu Leu Leu Asn Ala Glu Asn Pro Arg Gly Thr Phe Leu
                165                 170                 175
```

```
                                                              -continued gtg cga gaa agt gag acc acg aaa ggt gcc tac tgc ctc tca gtg tct        576
Val Arg Glu Ser Glu Thr Thr Lys Gly Ala Tyr Cys Leu Ser Val Ser
        180                 185                 190 gac ttc gac aac gcc aag ggc ctc aac gtg aag cac tac aag atc cgc        624
Asp Phe Asp Asn Ala Lys Gly Leu Asn Val Lys His Tyr Lys Ile Arg
    195                 200                 205 aag ctg gac agc ggc ggc ttc tac atc acc tcc cgc acc cag ttc aac        672
Lys Leu Asp Ser Gly Gly Phe Tyr Ile Thr Ser Arg Thr Gln Phe Asn
210                 215                 220 agc ctg cag cag ctg gtg gcc tac tac tcc aaa cac gcc gat ggc ctg        720
Ser Leu Gln Gln Leu Val Ala Tyr Tyr Ser Lys His Ala Asp Gly Leu
225                 230                 235                 240 tgc cac cgc ctc acc acc gtg tgc ccc acg tcc aag ccg cag act cag        768
Cys His Arg Leu Thr Thr Val Cys Pro Thr Ser Lys Pro Gln Thr Gln
                245                 250                 255 ggc ctg gcc aag gat gcc tgg gag atc cct cgg gag tcg ctg cgg ctg        816
Gly Leu Ala Lys Asp Ala Trp Glu Ile Pro Arg Glu Ser Leu Arg Leu
            260                 265                 270 gag gtc aag ctg ggc cag ggc tgc ttt ggc gag gtg tgg atg ggg acc        864
Glu Val Lys Leu Gly Gln Gly Cys Phe Gly Glu Val Trp Met Gly Thr
        275                 280                 285 tgg aac ggt acc acc agg gtg gcc atc aaa acc ctg aag cct ggc acg        912
Trp Asn Gly Thr Thr Arg Val Ala Ile Lys Thr Leu Lys Pro Gly Thr
    290                 295                 300 atg tct cca gag gcc ttc ctg cag gag gcc cag gtc atg aag aag ctg        960
Met Ser Pro Glu Ala Phe Leu Gln Glu Ala Gln Val Met Lys Lys Leu
305                 310                 315                 320 agg cat gag aag ctg gtg cag ttg tat gct gtg gtt tca gag gag ccc       1008
Arg His Glu Lys Leu Val Gln Leu Tyr Ala Val Val Ser Glu Glu Pro
                325                 330                 335 att tac atc gtc acg gag tac atg agc aag ggg agt ttg ctg gac ttt       1056
Ile Tyr Ile Val Thr Glu Tyr Met Ser Lys Gly Ser Leu Leu Asp Phe
            340                 345                 350 ctc aag ggg gag aca ggc aag tac ctg cgg ctg cct cag ctg gtg gac       1104
Leu Lys Gly Glu Thr Gly Lys Tyr Leu Arg Leu Pro Gln Leu Val Asp
        355                 360                 365 atg gct gct cag atc gcc tca ggc atg gcg tac gtg gag cgg atg aac       1152
Met Ala Ala Gln Ile Ala Ser Gly Met Ala Tyr Val Glu Arg Met Asn
    370                 375                 380 tac gtc cac cgg gac ctt cgt gca gcc aac atc ctg gtg gga gag aac       1200
Tyr Val His Arg Asp Leu Arg Ala Ala Asn Ile Leu Val Gly Glu Asn
385                 390                 395                 400 ctg gtg tgc aaa gtg gcc gac ttt ggg ctg gct cgg ctc att gaa gac       1248
Leu Val Cys Lys Val Ala Asp Phe Gly Leu Ala Arg Leu Ile Glu Asp
                405                 410                 415 aat gag tac acg gcg cgg caa ggt gcc aaa ttc ccc atc aag tgg acg       1296
Asn Glu Tyr Thr Ala Arg Gln Gly Ala Lys Phe Pro Ile Lys Trp Thr
            420                 425                 430 gct cca gaa gct gcc ctc tat ggc cgc ttc acc atc aag tcg gac gtg       1344
Ala Pro Glu Ala Ala Leu Tyr Gly Arg Phe Thr Ile Lys Ser Asp Val
        435                 440                 445 tgg tcc ttc ggg atc ctg ctg act gag ctc acc aca aag gga cgg gtg       1392
Trp Ser Phe Gly Ile Leu Leu Thr Glu Leu Thr Thr Lys Gly Arg Val
    450                 455                 460 ccc tac cct ggg atg gtg aac cgc gag gtg ctg gac cag gtg gag cgg       1440
Pro Tyr Pro Gly Met Val Asn Arg Glu Val Leu Asp Gln Val Glu Arg
465                 470                 475                 480 ggc tac cgg atg ccc tgc ccg ccg gag tgt ccc gag tcc ctg cac gac       1488
Gly Tyr Arg Met Pro Cys Pro Pro Glu Cys Pro Glu Ser Leu His Asp
                485                 490                 495
```

```
ctc atg tgc cag tgc tgg cgg aag gag cct gag gag cgg ccc acc ttc    1536
Leu Met Cys Gln Cys Trp Arg Lys Glu Pro Glu Glu Arg Pro Thr Phe
        500                 505                 510 gag tac ctg cag gcc ttc ctg gag gac tac ttc acg tcc acc gag ccc    1584
Glu Tyr Leu Gln Ala Phe Leu Glu Asp Tyr Phe Thr Ser Thr Glu Pro
        515                 520                 525 cag tac cag ccc ggg gag aac ctc tag                                1611
Gln Tyr Gln Pro Gly Glu Asn Leu
        530                 535

<210> SEQ ID NO 2
<211> LENGTH: 536
<212> TYPE: PRT
<213> ORGANISM: Homo sapiens
<220> FEATURE:
<221> NAME/KEY: MISC_FEATURE
<222> LOCATION: (1)..(536)
<223> OTHER INFORMATION: amino acid sequence of non-receptor tyrosine
      kinase encoded by the normal c-Src coding region

<400> SEQUENCE: 2

Met Gly Ser Asn Lys Ser Lys Pro Lys Asp Ala Ser Gln Arg Arg Arg
1               5                   10                  15

Ser Leu Glu Pro Ala Glu Asn Val His Gly Ala Gly Gly Gly Ala Phe
            20                  25                  30

Pro Ala Ser Gln Thr Pro Ser Lys Pro Ala Ser Ala Asp Gly His Arg
        35                  40                  45

Gly Pro Ser Ala Ala Phe Ala Pro Ala Ala Glu Pro Lys Leu Phe
    50                  55                  60

Gly Gly Phe Asn Ser Ser Asp Thr Val Thr Ser Pro Gln Arg Ala Gly
65                  70                  75                  80

Pro Leu Ala Gly Gly Val Thr Thr Phe Val Ala Leu Tyr Asp Tyr Glu
                85                  90                  95

Ser Arg Thr Glu Thr Asp Leu Ser Phe Lys Lys Gly Glu Arg Leu Gln
            100                 105                 110

Ile Val Asn Asn Thr Glu Gly Asp Trp Trp Leu Ala His Ser Leu Ser
        115                 120                 125

Thr Gly Gln Thr Gly Tyr Ile Pro Ser Asn Tyr Val Ala Pro Ser Asp
    130                 135                 140

Ser Ile Gln Ala Glu Glu Trp Tyr Phe Gly Lys Ile Thr Arg Arg Glu
145                 150                 155                 160

Ser Glu Arg Leu Leu Leu Asn Ala Glu Asn Pro Arg Gly Thr Phe Leu
                165                 170                 175

Val Arg Glu Ser Glu Thr Thr Lys Gly Ala Tyr Cys Leu Ser Val Ser
            180                 185                 190

Asp Phe Asp Asn Ala Lys Gly Leu Asn Val Lys His Tyr Lys Ile Arg
        195                 200                 205

Lys Leu Asp Ser Gly Gly Phe Tyr Ile Thr Ser Arg Thr Gln Phe Asn
    210                 215                 220

Ser Leu Gln Gln Leu Val Ala Tyr Tyr Ser Lys His Ala Asp Gly Leu
225                 230                 235                 240

Cys His Arg Leu Thr Thr Val Cys Pro Thr Ser Lys Pro Gln Thr Gln
                245                 250                 255

Gly Leu Ala Lys Asp Ala Trp Glu Ile Pro Arg Glu Ser Leu Arg Leu
            260                 265                 270

Glu Val Lys Leu Gly Gln Gly Cys Phe Gly Glu Val Trp Met Gly Thr
        275                 280                 285
```

```
Trp Asn Gly Thr Thr Arg Val Ala Ile Lys Thr Leu Lys Pro Gly Thr
    290                 295                 300

Met Ser Pro Glu Ala Phe Leu Gln Glu Ala Gln Val Met Lys Lys Leu
305                 310                 315                 320

Arg His Glu Lys Leu Val Gln Leu Tyr Ala Val Val Ser Glu Glu Pro
                325                 330                 335

Ile Tyr Ile Val Thr Glu Tyr Met Ser Lys Gly Ser Leu Leu Asp Phe
            340                 345                 350

Leu Lys Gly Glu Thr Gly Lys Tyr Leu Arg Leu Pro Gln Leu Val Asp
        355                 360                 365

Met Ala Ala Gln Ile Ala Ser Gly Met Ala Tyr Val Glu Arg Met Asn
    370                 375                 380

Tyr Val His Arg Asp Leu Arg Ala Ala Asn Ile Leu Val Gly Glu Asn
385                 390                 395                 400

Leu Val Cys Lys Val Ala Asp Phe Gly Leu Ala Arg Leu Ile Glu Asp
                405                 410                 415

Asn Glu Tyr Thr Ala Arg Gln Gly Ala Lys Phe Pro Ile Lys Trp Thr
            420                 425                 430

Ala Pro Glu Ala Ala Leu Tyr Gly Arg Phe Thr Ile Lys Ser Asp Val
        435                 440                 445

Trp Ser Phe Gly Ile Leu Leu Thr Glu Leu Thr Thr Lys Gly Arg Val
    450                 455                 460

Pro Tyr Pro Gly Met Val Asn Arg Glu Val Leu Asp Gln Val Glu Arg
465                 470                 475                 480

Gly Tyr Arg Met Pro Cys Pro Pro Glu Cys Pro Glu Ser Leu His Asp
                485                 490                 495

Leu Met Cys Gln Cys Trp Arg Lys Glu Pro Glu Glu Arg Pro Thr Phe
            500                 505                 510

Glu Tyr Leu Gln Ala Phe Leu Glu Asp Tyr Phe Thr Ser Thr Glu Pro
        515                 520                 525

Gln Tyr Gln Pro Gly Glu Asn Leu
    530                 535

<210> SEQ ID NO 3
<211> LENGTH: 1611
<212> TYPE: DNA
<213> ORGANISM: Homo sapiens
<220> FEATURE:
<221> NAME/KEY: misc_feature
<222> LOCATION: (1)..(1593)
<223> OTHER INFORMATION: nucleotide sequence of mutant c-Src oncogene
      coding region
<220> FEATURE:
<221> NAME/KEY: CDS
<222> LOCATION: (1)..(1593)
<223> OTHER INFORMATION:
<220> FEATURE:
<221> NAME/KEY: misc_feature
<222> LOCATION: (1591)..(1591)
<223> OTHER INFORMATION: Point mutation in normal c-Src causes
      transition from c-->t and the formation of a stop codon.

<400> SEQUENCE: 3 atg ggt agc aac aag agc aag ccc aag gat gcc agc cag cgg cgc cgc    48
Met Gly Ser Asn Lys Ser Lys Pro Lys Asp Ala Ser Gln Arg Arg Arg
1               5                   10                  15 agc ctg gag ccc gcc gag aac gtg cac ggc gct ggc ggg gct ttc        96
Ser Leu Glu Pro Ala Glu Asn Val His Gly Ala Gly Gly Ala Phe
            20                  25                  30
```

| | | |
|---|---|---|
| ccc gcc tcg cag acc ccc agc aag cca gcc tcg gcc gac ggc cac cgc<br>Pro Ala Ser Gln Thr Pro Ser Lys Pro Ala Ser Ala Asp Gly His Arg<br>35 40 45 | 144 | |
| ggc ccc agc gcg gcc ttc gcc ccc gcg gcc gcc gag ccc aag ctg ttc<br>Gly Pro Ser Ala Ala Phe Ala Pro Ala Ala Ala Glu Pro Lys Leu Phe<br>50 55 60 | 192 | |
| gga ggc ttc aac tcc tcg gac acc gtc acc tcc ccg cag agg gcg ggc<br>Gly Gly Phe Asn Ser Ser Asp Thr Val Thr Ser Pro Gln Arg Ala Gly<br>65 70 75 80 | 240 | |
| ccg ctg gcc ggt gga gtg acc acc ttt gtg gcc ctc tat gac tat gag<br>Pro Leu Ala Gly Gly Val Thr Thr Phe Val Ala Leu Tyr Asp Tyr Glu<br>85 90 95 | 288 | |
| tct agg acg gag aca gac ctg tcc ttc aag aaa ggc gag cgg ctc cag<br>Ser Arg Thr Glu Thr Asp Leu Ser Phe Lys Lys Gly Glu Arg Leu Gln<br>100 105 110 | 336 | |
| att gtc aac aac acg gag gga gac tgg tgg ctg gcc cac tcg ctc agc<br>Ile Val Asn Asn Thr Glu Gly Asp Trp Trp Leu Ala His Ser Leu Ser<br>115 120 125 | 384 | |
| aca gga cag aca ggc tac atc ccc agc aac tac gtg gcg ccc tcc gac<br>Thr Gly Gln Thr Gly Tyr Ile Pro Ser Asn Tyr Val Ala Pro Ser Asp<br>130 135 140 | 432 | |
| tcc atc cag gct gag gag tgg tat ttt ggc aag atc acc aga cgg gag<br>Ser Ile Gln Ala Glu Glu Trp Tyr Phe Gly Lys Ile Thr Arg Arg Glu<br>145 150 155 160 | 480 | |
| tca gag cgg tta ctg ctc aat gca gag aac ccg aga ggg acc ttc ctc<br>Ser Glu Arg Leu Leu Leu Asn Ala Glu Asn Pro Arg Gly Thr Phe Leu<br>165 170 175 | 528 | |
| gtg cga gaa agt gag acc acg aaa ggt gcc tac tgc ctc tca gtg tct<br>Val Arg Glu Ser Glu Thr Thr Lys Gly Ala Tyr Cys Leu Ser Val Ser<br>180 185 190 | 576 | |
| gac ttc gac aac gcc aag ggc ctc aac gtg aag cac tac aag atc cgc<br>Asp Phe Asp Asn Ala Lys Gly Leu Asn Val Lys His Tyr Lys Ile Arg<br>195 200 205 | 624 | |
| aag ctg gac agc ggc ggc ttc tac atc acc tcc cgc acc cag ttc aac<br>Lys Leu Asp Ser Gly Gly Phe Tyr Ile Thr Ser Arg Thr Gln Phe Asn<br>210 215 220 | 672 | |
| agc ctg cag cag ctg gtg gcc tac tac tcc aaa cac gcc gat ggc ctg<br>Ser Leu Gln Gln Leu Val Ala Tyr Tyr Ser Lys His Ala Asp Gly Leu<br>225 230 235 240 | 720 | |
| tgc cac cgc ctc acc acc gtg tgc ccc acg tcc aag ccg cag act cag<br>Cys His Arg Leu Thr Thr Val Cys Pro Thr Ser Lys Pro Gln Thr Gln<br>245 250 255 | 768 | |
| ggc ctg gcc aag gat gcc tgg gag atc cct cgg gag tcg ctg cgg ctg<br>Gly Leu Ala Lys Asp Ala Trp Glu Ile Pro Arg Glu Ser Leu Arg Leu<br>260 265 270 | 816 | |
| gag gtc aag ctg ggc cag ggc tgc ttt ggc gag gtg tgg atg ggg acc<br>Glu Val Lys Leu Gly Gln Gly Cys Phe Gly Glu Val Trp Met Gly Thr<br>275 280 285 | 864 | |
| tgg aac ggt acc acc agg gtg gcc atc aaa acc ctg aag cct ggc acg<br>Trp Asn Gly Thr Thr Arg Val Ala Ile Lys Thr Leu Lys Pro Gly Thr<br>290 295 300 | 912 | |
| atg tct cca gag gcc ttc ctg cag gag gcc cag gtc atg aag aag ctg<br>Met Ser Pro Glu Ala Phe Leu Gln Glu Ala Gln Val Met Lys Lys Leu<br>305 310 315 320 | 960 | |
| agg cat gag aag ctg gtg cag ttg tat gct gtg gtt tca gag gag ccc<br>Arg His Glu Lys Leu Val Gln Leu Tyr Ala Val Val Ser Glu Glu Pro<br>325 330 335 | 1008 | |
| att tac atc gtc acg gag tac atg agc aag ggg agt ttg ctg gac ttt<br>Ile Tyr Ile Val Thr Glu Tyr Met Ser Lys Gly Ser Leu Leu Asp Phe<br>340 345 350 | 1056 | |

```
ctc aag ggg gag aca ggc aag tac ctg cgg ctg cct cag ctg gtg gac    1104
Leu Lys Gly Glu Thr Gly Lys Tyr Leu Arg Leu Pro Gln Leu Val Asp
        355                 360                 365 atg gct gct cag atc gcc tca ggc atg gcg tac gtg gag cgg atg aac    1152
Met Ala Ala Gln Ile Ala Ser Gly Met Ala Tyr Val Glu Arg Met Asn
    370                 375                 380 tac gtc cac cgg gac ctt cgt gca gcc aac atc ctg gtg gga gag aac    1200
Tyr Val His Arg Asp Leu Arg Ala Ala Asn Ile Leu Val Gly Glu Asn
385                 390                 395                 400 ctg gtg tgc aaa gtg gcc gac ttt ggg ctg gct cgg ctc att gaa gac    1248
Leu Val Cys Lys Val Ala Asp Phe Gly Leu Ala Arg Leu Ile Glu Asp
                405                 410                 415 aat gag tac acg gcg cgg caa ggt gcc aaa ttc ccc atc aag tgg acg    1296
Asn Glu Tyr Thr Ala Arg Gln Gly Ala Lys Phe Pro Ile Lys Trp Thr
            420                 425                 430 gct cca gaa gct gcc ctc tat ggc cgc ttc acc atc aag tcg gac gtg    1344
Ala Pro Glu Ala Ala Leu Tyr Gly Arg Phe Thr Ile Lys Ser Asp Val
        435                 440                 445 tgg tcc ttc ggg atc ctg ctg act gag ctc acc aca aag gga cgg gtg    1392
Trp Ser Phe Gly Ile Leu Leu Thr Glu Leu Thr Thr Lys Gly Arg Val
    450                 455                 460 ccc tac cct ggg atg gtg aac cgc gag gtg ctg gac cag gtg gag cgg    1440
Pro Tyr Pro Gly Met Val Asn Arg Glu Val Leu Asp Gln Val Glu Arg
465                 470                 475                 480 ggc tac cgg atg ccc tgc ccg ccg gag tgt ccc gag tcc ctg cac gac    1488
Gly Tyr Arg Met Pro Cys Pro Pro Glu Cys Pro Glu Ser Leu His Asp
                485                 490                 495 ctc atg tgc cag tgc tgg cgg aag gag cct gag gag cgg ccc acc ttc    1536
Leu Met Cys Gln Cys Trp Arg Lys Glu Pro Glu Glu Arg Pro Thr Phe
            500                 505                 510 gag tac ctg cag gcc ttc ctg gag gac tac ttc acg tcc acc gag ccc    1584
Glu Tyr Leu Gln Ala Phe Leu Glu Asp Tyr Phe Thr Ser Thr Glu Pro
        515                 520                 525 cag tac tag cccggggaga acctctag                                    1611
Gln Tyr
    530

<210> SEQ ID NO 4
<211> LENGTH: 530
<212> TYPE: PRT
<213> ORGANISM: Homo sapiens
<220> FEATURE:
<221> NAME/KEY: MISC_FEATURE
<222> LOCATION: (1)..(530)
<223> OTHER INFORMATION: amino acid sequence of the mutant c-Src
      polypeptide encoded by the mutant c-Src coding region

<400> SEQUENCE: 4

Met Gly Ser Asn Lys Ser Lys Pro Lys Asp Ala Ser Gln Arg Arg Arg
1               5                   10                  15

Ser Leu Glu Pro Ala Glu Asn Val His Gly Ala Gly Gly Gly Ala Phe
            20                  25                  30

Pro Ala Ser Gln Thr Pro Ser Lys Pro Ala Ser Ala Asp Gly His Arg
        35                  40                  45

Gly Pro Ser Ala Ala Phe Ala Pro Ala Ala Glu Pro Lys Leu Phe
    50                  55                  60

Gly Gly Phe Asn Ser Ser Asp Thr Val Thr Ser Pro Gln Arg Ala Gly
65                  70                  75                  80

Pro Leu Ala Gly Gly Val Thr Thr Phe Val Ala Leu Tyr Asp Tyr Glu
                85                  90                  95
```

-continued

```
Ser Arg Thr Glu Thr Asp Leu Ser Phe Lys Lys Gly Glu Arg Leu Gln
            100                 105                 110

Ile Val Asn Asn Thr Glu Gly Asp Trp Trp Leu Ala His Ser Leu Ser
            115                 120                 125

Thr Gly Gln Thr Gly Tyr Ile Pro Ser Asn Tyr Val Ala Pro Ser Asp
            130                 135                 140

Ser Ile Gln Ala Glu Glu Trp Tyr Phe Gly Lys Ile Thr Arg Arg Glu
145                 150                 155                 160

Ser Glu Arg Leu Leu Leu Asn Ala Glu Asn Pro Arg Gly Thr Phe Leu
                165                 170                 175

Val Arg Glu Ser Glu Thr Thr Lys Gly Ala Tyr Cys Leu Ser Val Ser
            180                 185                 190

Asp Phe Asp Asn Ala Lys Gly Leu Asn Val Lys His Tyr Lys Ile Arg
            195                 200                 205

Lys Leu Asp Ser Gly Gly Phe Tyr Ile Thr Ser Arg Thr Gln Phe Asn
            210                 215                 220

Ser Leu Gln Gln Leu Val Ala Tyr Tyr Ser Lys His Ala Asp Gly Leu
225                 230                 235                 240

Cys His Arg Leu Thr Thr Val Cys Pro Thr Ser Lys Pro Gln Thr Gln
                245                 250                 255

Gly Leu Ala Lys Asp Ala Trp Glu Ile Pro Arg Glu Ser Leu Arg Leu
            260                 265                 270

Glu Val Lys Leu Gly Gln Gly Cys Phe Gly Glu Val Trp Met Gly Thr
            275                 280                 285

Trp Asn Gly Thr Thr Arg Val Ala Ile Lys Thr Leu Lys Pro Gly Thr
            290                 295                 300

Met Ser Pro Glu Ala Phe Leu Gln Glu Ala Gln Val Met Lys Lys Leu
305                 310                 315                 320

Arg His Glu Lys Leu Val Gln Leu Tyr Ala Val Val Ser Glu Glu Pro
                325                 330                 335

Ile Tyr Ile Val Thr Glu Tyr Met Ser Lys Gly Ser Leu Leu Asp Phe
            340                 345                 350

Leu Lys Gly Glu Thr Gly Lys Tyr Leu Arg Leu Pro Gln Leu Val Asp
            355                 360                 365

Met Ala Ala Gln Ile Ala Ser Gly Met Ala Tyr Val Glu Arg Met Asn
            370                 375                 380

Tyr Val His Arg Asp Leu Arg Ala Ala Asn Ile Leu Val Gly Glu Asn
385                 390                 395                 400

Leu Val Cys Lys Val Ala Asp Phe Gly Leu Ala Arg Leu Ile Glu Asp
                405                 410                 415

Asn Glu Tyr Thr Ala Arg Gln Gly Ala Lys Phe Pro Ile Lys Trp Thr
            420                 425                 430

Ala Pro Glu Ala Ala Leu Tyr Gly Arg Phe Thr Ile Lys Ser Asp Val
            435                 440                 445

Trp Ser Phe Gly Ile Leu Leu Thr Glu Leu Thr Thr Lys Gly Arg Val
450                 455                 460

Pro Tyr Pro Gly Met Val Asn Arg Glu Val Leu Asp Gln Val Glu Arg
465                 470                 475                 480

Gly Tyr Arg Met Pro Cys Pro Pro Glu Cys Pro Glu Ser Leu His Asp
                485                 490                 495

Leu Met Cys Gln Cys Trp Arg Lys Glu Pro Glu Glu Arg Pro Thr Phe
            500                 505                 510
```

```
Glu Tyr Leu Gln Ala Phe Leu Glu Asp Tyr Phe Thr Ser Thr Glu Pro
        515                 520                 525
Gln Tyr
    530

<210> SEQ ID NO 5
<211> LENGTH: 20
<212> TYPE: DNA
<213> ORGANISM: Artificial Sequence
<220> FEATURE:
<223> OTHER INFORMATION: 3' mutant allele specific primer
<220> FEATURE:
<221> NAME/KEY: misc_feature
<222> LOCATION: (15)..(15)
<223> OTHER INFORMATION: n is defined as a 3-nitropyrrole residue

<400> SEQUENCE: 5
tagaggttct ccccnggcta                                                20

<210> SEQ ID NO 6
<211> LENGTH: 20
<212> TYPE: DNA
<213> ORGANISM: Artificial Sequence
<220> FEATURE:
<223> OTHER INFORMATION: 3' wild-type allele specific primer

<400> SEQUENCE: 6
tagaggttct ccccgggctg                                                20

<210> SEQ ID NO 7
<211> LENGTH: 164
<212> TYPE: DNA
<213> ORGANISM: Artificial Sequence
<220> FEATURE:
<223> OTHER INFORMATION: Antisense sequence complementary to 5' region
      of c-Src gene

<400> SEQUENCE: 7
gccccgcagg tgcctactgc ctctcagtgt ctgacttcga caacgccaag ggcctcaacg      60
tgaagcacta caagatccgc aagctggaca gcggcggctt ctacatcacc tcccgcaccc    120
agttcaacag cctgcagcag ctggtggcct actactccag tgag                    164
```

MUTATED SRC ONCOGENE COMPOSITION AND METHODS

CROSS-REFERENCE TO RELATED APPLICATION

The present application is a continuation of U.S. application Ser. No. 09/444,711, filed Nov. 24, 1999, now U.S. Pat. No. 6,764,833 which is hereby incorporated by reference herein in its entirety, including all figures, tables, nucleic acid sequences, amino acid sequences, and drawings.

The development of this invention was supported by NIH grants CA65512 and CA55652. Accordingly, the United States Government has certain rights in this invention.

1. FIELD OF THE INVENTION

This invention relates to a newly identified Src oncogene mutation, polypeptides containing such mutation, and polynucleotides encoding such mutation. This invention also relates to methods of identifying the Src mutation, to the use of such methods in therapy and diagnosis, and to methods of identifying agonist and antagonist compounds useful for treating and/or preventing clinical conditions associated with or caused by Src mutation. Methods and compositions are provided for identifying and treating malignant cells in a host such as human. Mutated DNA sequence probes and primers are made for determining the expression of mutated nucleic acid.

2. BACKGROUND OF THE INVENTION

The discovery of Rous sarcoma virus (RSV) led to the identification of a cellular oncogene Src (c-Src) (SEQ ID NO. 1), which encodes a non-receptor tyrosine kinase (phosphoprotein of molecular weight 60,000 Dalton or pp60c-Src) (SEQ ID NO. 2). The Src oncogene has been implicated in the development of numerous types of cancers via a yet to be elucidated mechanism (see for example Stehelin, D., Varmus, H. E., Bishop, J. M. & Vogt, P. K. Nature 260, 170–173 (1976); Brugge, J. S. & Erikson, R. L. Identification of a transformation-specific antigen induced by an avian sarcoma virus. Nature 269, 346–348 (1977); Jove, R. & Hanafusa, H. Cell transformation by the viral Src oncogene. Annu Rev Cell Biol 3, 31–56 (1987); Thomas, S. M. & Brugge, J. S. Cellular functions regulated by Src family kinases. Annu Rev Cell Dev Biol 13, 513–609 (1997)). The nucleic acid sequence of normal c-Src is as follows:

```
atgggtagca acaagagcaa gcccaaggat gccagccagc ggcgccgcag cctggagccc    60
gccgagaacg tgcacggcgc tggcggggggc gctttccccg cctcgcagac ccccagcaag   120
ccagcctcgg ccgacggcca ccgcggcccc agcgcggcct tcgccccccgc ggccgccgag   180 cccaagctgt tcggaggctt caactcctcg gacaccgtca cctccccgca gagggcgggc   240
ccgctggccg gtggagtgac caccttgtgt gccctctatg actatgagtc taggacggag   300
acagacctgt ccttcaagaa aggcgagcgg ctccagattg tcaacaacac ggagggagac   360
tggtggctgg cccactcgct cagcacagga cagacaggct acatccccag caactacgtg   420
gcgccctccg actccatcca ggctgaggag tggtattttg gcaagatcac cagacgggag   480
tcagagcggt tactgctcaa tgcagagaac ccgagaggga ccttcctcgt gcgagaaagt   540
gagaccacga aggtgcccta ctgcctctca gtgtctgact tcgacaacgc caagggcctc   600
aacgtgaagc actacaagat ccgcaagctg gacagcggcg gcttctacat cacctcccgc   660
acccagttca acagcctgca gcagctggtg gcctactact ccaaacacgc cgatggcctg   720
tgccaccgcc tcaccaccgt gtgccccacg tccaagccgc agactcaggg cctggccaag   780
gatgcctggg agatccctcg ggagtcgctg cggctggagg tcaagctggg ccagggctgc   840
tttggcgagg tgtggatggg gacctggaac ggtaccacca gggtggccat caaaaccctg   900
aagcctggca cgatgtctcc agaggccttc ctgcaggagg cccaggtcat gaagaagctg   960
aggcatgaga agctggtgca gttgtatgct gtggtttcag aggagcccat ttacatcgtc  1020
acggagtaca tgagcaaggg gagtttgctg gactttctca aggggagac aggcaagtac  1080 ctgcggctgc ctcagctggt ggacatggct gctcagatcg cctcaggcat ggcgtacgtg  1140
gagcggatga actacgtcca ccgggacctt cgtgcagcca acatcctggt gggagagaac  1200
ctggtgtgca aagtggccga ctttgggctg gctcggctca ttgaagacaa tgagtacacg  1260
gcgcggcaag gtgccaaatt ccccatcaag tggacggctc cagaagctgc cctctatggc  1320
cgcttcacca tcaagtcgga cgtgtggtcc ttcggatcc tgctgactga gctcaccaca  1380
aagggacggg tgccctaccc tgggatggtg aaccgcgagg tgctggacca ggtggagcgg  1440
```

```
                                      -continued
ggctaccgga tgccctgccc gccggagtgt cccgagtccc tgcacgacct catgtgccag   1500
tgctggcgga aggagcctga ggagcggccc accttcgagt acctgcaggc cttcctggag   1560
gactacttca cgtccaccga gccccagtac cagcccgggg agaacctcta g            1611

(SEQ ID NO: 1)
```

The c-Src nucleic acid sequence (SEQ ID NO. 1) encodes for a tyrosine kinase protein pp60, which has a following sequence:

```
  1 MGSNKSKPKD ASQRRRSLEP AENVHGAGGG AFPASQTPSK PASADGHRGP SAAFAPAAAE

61 PKLFGGFNSS DTVTSPQRAG PLAGGVTTFV ALYDYESRTE TDLSFKKGER LQIVNNTEGD

121 WWLAHSLSTG QTGYIPSNYV APSDSIQAEE WYFGKITRRE SERLLLNAEN PRGTFLVRES

181 ETTKGAYCLS VSDFDNAKGL NVKHYKIRKL DSGGFYITSR TQFNSLQQLV AYYSKHADGL

241 CHRLTTVCPT SKPQTQGLAK DAWEIPRESL RLEVKLGQGC FGEVWMGTWN GTTRVAIKTL

301 KPGTMSPEAF LQEAQVMKKL RHEKLVQLYA VVSEEPIYIV TEYMSKGSLL DFLKGETGKY

361 LRLPQLVDMA AQIASGMAYV ERMNYVHRDL RAANILVGEN LVCKVADFGL ARLIEDNEYT

421 ARQGAKFPIK WTAPEAALYG RFTIKSDVWS FGILLTELTT KGRVPYPGMV NREVLDQVER

481 GYRMPCPPEC PESLHDLMCQ CWRKEPEERP TFEYLQAFLE DYFTSTEPQY

531 QPGENL (SEQ ID NO: 2)
```

Amino acids are abbreviated as 1-letter codes and corresponding 3-letter codes as follows: Alanine is A or Ala; Arginine R or Arg, Asparagine N or Asn; Aspartic acid D or Asp; Cysteine C or Cys; Glutamine Q or Gln; Glutamic acid E or Glu; Glycine G or Gly; Histidine H or His; Isoleucine I or Ile; Leucine L or Leu; Lysine K or Lys; Methionine M or Met; Phenylalanine F or Phe; Proline P or Pro; Serine S or Ser; Threonine T or Thr; Tryptophan W or Trp; Tyrosine Y or Tyr; and Valine V or Val.

The cellular Src oncogene (c-Src) (SEQ ID NO. 1) is the normal counterpart of the transforming viral Rous sarcoma oncogene (v-Src). v-Src has been shown to induce the production of specific metalloproteinases (Hamaguchi, M. et al. Augmentation of metalloproteinase (gelatinase) activity secreted from Rous sarcoma virus-infected cells correlates with transforming activity of Src. Oncogene 10, 1037–1043 (1995)) and to foster the metastatic phenotype (Egan, S. et al. Transformation by oncogenes encoding protein kinases induces the metastatic phenotype. Science 238 202–205 (1987); Tatsuka, M. et al. Different metastatic potentials of ras- and Src-transformed BALB/c 3T3 A31 variant cells. Mol. Carcinog. 15, 300–308 (1996)). However, as opposed to cellular c-Src (SEQ ID NO. 1) the retroviral v-Src has 19 C-terminal residues replaced by a sequence of 12 amino acids, lacking the regulatory tyrosine.

The non receptor tyrosine kinase c-Src consists of an SH3, SH2 and tyrosine kinase domain. c-Src appears to be the most important to the normal function of osteoclasts, as determined from studies of Src-knock-out mice (see for example U.S. Pat. No. 5,541,109). The catalytic activity of c-Src and other nonreceptor tyrosine kinases is inhibited by the intramolecular association of their intrinsic SH2 domain to the carboxy-terminal tail upon phosphorylation of Tyr (position 530, avian position 527). Protein tyrosine phosphorylation is believed to be an important regulatory event in cell growth and differentiation. Phosphorylation on tyrosine can either decrease or increase the enzymatic activity of substrate proteins. Tyrosine phosphorylated sequences associate with Src homology 2 (SH2) domains, and thus tyrosine phosphorylation also serves to regulate protein/protein interactions. Many protein tyrosine kinases have been described to date: several are the receptors for peptide growth factors; others are expressed in the cytoplasm and nucleus. Tyrosine kinases can be of the receptor type (having extracellular, transmembrane and intracellular domains) or the non-receptor type (being wholly intracellular). There are 19 known families of receptor tyrosine kinases including the Her family (EGFR, Her 2, Her 3, Her 4), the insulin receptor family (insulin receptor, IGF-1R, insulin-related receptor), the PDGF receptor family (PDGF-R alpha and beta, CSF-1R, Kit, Flk2), the Flk family (Flk-1, Flt-1, Flk-4), the FGF-receptor family (FGF-Rs 1 through 4), the Met family (Met, Ron), etc. There are 11 known families of non-receptor type tyrosine kinases including the Src family (Src, Yes, Fyn, Lyn, Lck, Blk, Hck, Fgr, Yrk), Abl family (Abl, Arg), Zap 70 family (Zap 70, Syk) and Jak family (Jak 1, Jak 2, Tyk 2, Jak 3). Many of these tyrosine kinases have been found to be involved in cellular signaling pathways leading to pathogenic conditions such as cancer, psoriasis, hyperimmune response, etc. Other roles for tyrosine kinases include cellular responses to a variety of extracellular signals, such as those arising from growth factors and cell-cell interactions, as well as in differentiating developmental processes in both vertebrates and invertebrates.

Among various types of tumors, e.g., sarcoma, neuroblastoma, breast carcinoma among many others, c-Src has been found to be activated, particularly in colon cancers, especially in those metastatic to the liver (Rosen, N. et al. Analysis of pp60c-Src protein kinase activity in human tumor cell lines and tissues. J Biol Chem 261, 13754–13759 (1986); Bolen, J., Veillette, A., Schwartz, A., DeSeau, V. & Rosen, N. Activation of pp60c-Src protein kinase activity in human colon carcinoma. Proc. Natl Acad. Sci. U S A 84, 2251–2255 (1987); Cartwright, C., Kamps, M., Meisler, A., Pipas, J. & Eckhart, W. pp60c-Src activation in human colon carcinoma. J. Clin. Invest. 83, 2025–2033 (1989); Talamonti, M. A., Roh, M. S., Curley, S. A. & Gallick, G. E. Increase in activity and level of pp60c-Src in progressive stages of human colorectal cancer. J. Clin. Invest. 91, 53–60 (1991); Cartwright, C., Coad, C. & Egbert, B. Elevated c-Src tyrosine kinase activity in premalignant epithelia of ulcerative colitis. J. Clin. Invest. 93, 509–515 (1994); Termuhlen, P. M., Curley, S. A., Talamonti, M. S., Saboorian, M. H. & Gallick, G.E. Site-specific differences in pp60c-Src activity in human colorectal metastases. J. Surg. Res. 54, 293–298 (1993); Mao, W. et al. Activation of c-Src by receptor tyrosine kinases in human colon cancer cells with high metastatic potential. Oncogene 15, 3083–3090 (1997)).

Studies of the mechanism of c-Src regulation have suggested that c-Src kinase activity can be downregulated by phosphorylation of an amino acid tyrosine at position 530 (Tyr 530 in human c-Src, which is equivalent to Tyr 527 in chicken Src) of the C-terminal regulatory region (Cooper, J., Gould, K., Cartwright, C. & Hunter, T. Tyr 527 is phosphorylated in pp60c-Src: implications for regulation. Science 231, 1431–1434 (1986); Cartwright, C., Eckhart, W., Simon, S. & Kaplan, P. Cell transformation by pp60c-Src mutated in the carboxy-terminal regulatory domain. Cell 49,83–91 (1987); Kmiecik, T. & Shalloway, D. Activation and suppression of pp60c-Src transforming ability by mutation of its primary sites of tyrosine phosphorylation. Cell 49,65–73 (1987); Piwnica-Worms, H., Saunders, K. B., Roberts, T. M., Smith, A. E. & Cheng, S. H. Tyrosine phosphorylation regulates the biochemical and biological properties of pp60c-Src. Cell 49, 75–82 (1987); Reynolds, A. B. et al. Activation of the oncogenic potential of the avian cellular Src protein by specific structural alteration of the carboxy terminus. Embo J. 6, 2359–2364 (1987); Jove, R., Hanafusa, T., Hamaguchi, M. & Hanafusa, H. In vivo phosphorylation states and kinase activities of transforming p60c-Src mutants. Oncogene Res. 5,49–60(1989); Bjorge, J. et al. Characterization of two activated mutants of human pp60c-Src that escape c-Src kinase regulation by distinct mechanisms. J. Biol. Chem. 270, 24222–24228 (1995)). It is possible that other mutations and phosphorylation processes involving tyrosine and other amino acids encoded by Src oncogene might be linked to tumorigenesis. For example, in chickens a single point mutation at residues Thr 338, Glu 378, Ile 441 or Arg 95 appears to activate the transforming ability of pp60c-Src (Wang P, Fromowitz F, Koslow M, Hagag N, Johnson B, Viola M. c-Src structure in human cancers with elevated pp60c-Src activity. Br J Cancer Sep; 64(3):531–3, 1991). However, according to the current state of the art, nothing has been identified in the human species that is as important as phosphorylation of Tyr 530 residue. For example, phosphorylation of Tyr 419 is not essential for tumor transformation (Snyder, M. A., Bishop, J. M., Colby, W. W. & Levinson, A. D. Phosphorylation of tyrosine-416 is not required for the transforming properties and kinase activity of pp60v-Src. Cell 32, 891–901 (1983)). While this Tyr 530 mutation might be responsible for tumor formation it may not be the only cause and there is thus a continuing need to identify and further characterize the c-Src gene and pp60 as targets for drug discovery. The present inventors have surprisingly discovered for the first time that a novel mutation at SRC 531 is responsible for malignant transformation and metastasis. The existence of a mutant form of c-Src (SEQ ID NO. 3) is disclosed that plays a role in Src activation in cancer.

3. SUMMARY OF THE INVENTION

The present invention relates to mutated c-Src, in particular to Src polynucleotides and c-Src polypeptides and methods of using them in fields of diagnosis, therapy, and prevention arts. More specifically, the present invention provides a recombinant nucleic acid or oligonucleotide consisting essentially of SEQ ID NO. 3 and a polypeptide encoded by this nucleic acid (SEQ ID NO. 4). The oligonucleotide having a sequence complementary to the SEQ ID NO. 3 is also provided. Preferably the c-Src oncogene of the invention is truncated and preferably this truncation occurs at the 3' end. As a result of the truncation the expression of truncated c-Src preferably results in loss of one or more amino acids in the C-terminal end of phosphoprotein pp60c-Src. An isolated DNA molecule is contemplated which comprises a nucleic acid sequence encoding a mutated protein comprising Src protein tyrosine kinase activity, lacking the carboxy-terminal end. Also contemplated is an isolated nucleic acid consisting of the nucleotide sequence of SEQ ID NO. 3 or a contiguous fragment thereof wherein said isolated nucleic acid encodes a polypeptide having the biological activity of tyrosine kinase protein. Also contemplated is an isolated nucleic acid consisting of a nucleotide sequence that is at least 90% identical to the nucleotide sequence of SEQ ID NO. 3.

The instant invention also provides a polypeptide of about 400 to 530 amino acids in length and having at least 80% amino acid homology to the mutated c-Src 531 polypeptide of SEQ ID NO. 4 wherein said homologous polypeptide displays tyrosine kinase activity. Accordingly, methods are provided for producing and purifying these polypeptides. These methods include the steps of culturing the c-Src mutant transformed host cell under conditions suitable for the expression of the polypeptide and recovering the mutant c-Src polypeptide from the host cell or the host cell culture.

This invention also provides a method of screening agonist and antagonist compounds for the treatment of mutant Src associated or caused diseases. A method of treating a cancer is provided by administering to cancerous cells exhibiting a c-Src mutation at SRC 531 an effective amount of a compound capable of inhibiting the excess kinase activity resulting from the c-Src mutation or capable of inhibiting expression of the c-Src mutant gene (SEQ ID NO. 3). Preferred compounds of the invention comprise an antisense oligonucleotide, or a preparation of antibodies, or other molecules which specifically bind to c-Src SRC 531 mutant (SEQ ID NO. 3).

Various methods are provided for detecting the presence of SRC 531 mutation in Src oncogene contained in a sample. Such methods can include contacting the sample with two primers that are upstream and downstream of SRC 531 region, amplifying the SRC 531 region according to standard procedures, and detecting whether the amplified sequence is present or absent in the nucleic acid sample. Accordingly primers capable of recognizing and binding to SRC 531 region and nucleic acid probes having an affinity to SRC 531 mutated region of Src oncogene are preferred means of supporting such methods. Without limiting to these diagnostic methods a method is provided for detecting SRC 531 mutation whereby a restriction enzyme Sca I is used to recognize the lack or presence of restriction site at the mutated codon. Thus, also envisioned in the present invention is a diagnostic kit for detecting mutant Src oncogene related malignancy in an animal. Such a kit preferably comprises multiple containers wherein included is a set of primers useful for PCR detection of the mutated region of Src oncogene, and optionally a positive control comprising mutated Src sequence and a negative control comprising a non-mutated Src sequence.

The present invention also comprises a transgenic animal such as a mouse whose somatic and germ cells contain a gene (SEQ ID NO. 3) encoding for SRC 531 (SEQ ID NO. 4), said gene operably linked to a promoter, wherein expression of said SRC 531 gene results in the formation of inborn abnormalities or tumors in the mouse.

Preferably, a composition comprising the c-Src mutant polypeptide (SEQ ID NO. 4) is provided in combination with an immune adjuvant. This composition serves as a cancer vaccine comprising as an immunogen at least one immunogenic epitope of the SRC 531 mutant protein.

4. BRIEF DESCRIPTION OF THE DRAWINGS

FIG. 1. illustrates identification of the SRC 531 mutation in human tumors. a, Direct sequence analysis depicting the C->T mutation. While the genomic mutation is heterozygous, a manual sequencing gel derived from cloned PCR products is shown. b and c, RFLP analysis of PCR products from liver metastases (LM) and primary tumors that metastasized distantly to the liver and other organs (Dukes' stage D) tumors and normal matched tissues. The uncut 248 bp product is indicated as well as the 188 bp cut band when present. Negative control reflects normal DNA; positive control reflects plasmid bearing the SRC 531 mutation. d, Src kinase assay indicating that tumors with the SRC 531 mutation also display increased kinase activity.

Figure 2:
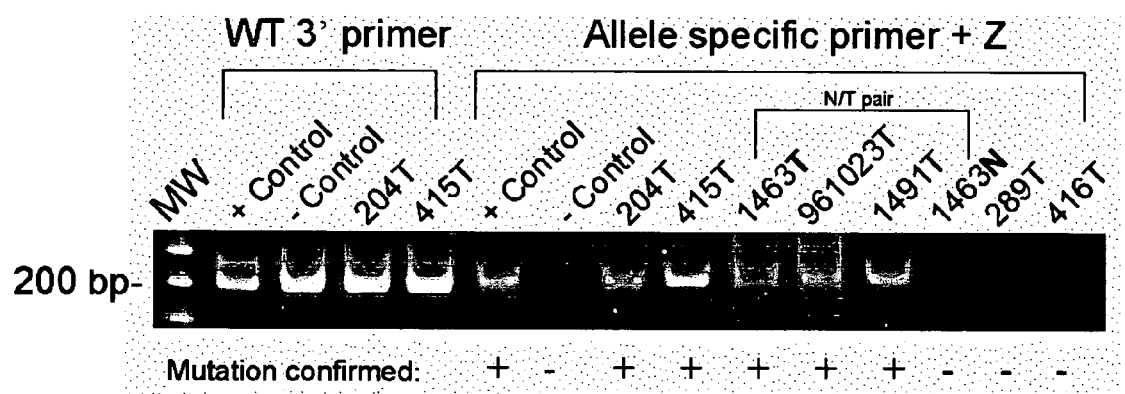

FIG. 2. illustrates confirmation of SRC 531 mutation in tumors by mutant allele specific PCR.

FIG. 3. illustrates kinase activity and phosphorylation phosphotyrosine analysis sites of normal and mutant Src proteins. a, Lysates from cells transfected with empty vector, c-Src vector (wild type), SRC 531 vector or v-Src vector are immunoprecipitated and subjected to kinase assays of autophosphorylation and phosphorylation of the exogenous substrate, enolase. b and c, Comparison of kinase activity phosphotyrosine levels with Src protein levels in wild type and mock, c-Src, SRC 531, or v-Src transfected cells using phosphotyrosine Western blot analyses. Human colon cancer cells transfected with c-Src (KM12C-c-Src) are shown for comparison. d, CNBr cleavage mapping indicates the sites of phosphorylation of c-Src, SRC 531, and v-Src.

FIG. 4 illustrates analysis of fibroblasts transfected with the SRC 531 expression construct for cellular transformation and metastatic potential. a, Soft agar assay demonstrates anchorage independent growth in cells transfected with v-Src and SRC 531 but not c-Src. b, Photograph depicting v-Src and SRC 531 clones growing in soft agar. Transfectants expressing SRC 531 produced smaller colonies. c, Analysis of capacity of various transfected cells to produce foci as a measure of cellular transformation independent of clonal variation artifact. d, Evidence for invasive activity of fibroblasts transfected with either v-Src or SRC 531 expression constructs versus c-Src as control. e, Survival analysis of mice injected with 1×105 cells/0.1 ml I.V. in an experimental lung metastasis assay. Photomicrographs inset show histology of lung tumors that formed in mice injected with v-Src and SRC 531 transfectants.

BRIEF DESCRIPTION OF THE SEQUENCES

SEQ ID NO. 1 is the normal or wild-type cellular oncogene Src (c-Src).

SEQ ID NO. 2 is the non-receptor tyrosine kinase (phosphoprotein of molecular weight 60,000 Dalton or pp60c-Src; 536 amino acids long) encoded by the wild-type c-Src (SEQ ID NO. 1).

SEQ ID NO. 3 is a mutant form of the c-Src oncogene, having a C→T transition mutation at nucleotide 1591, thereby encoding a stop signal (-uag-) at codon 531 (corresponding to nucleotides 1591–1593).

SEQ ID NO. 4 is the mutant (fruncated) c-Src 531 polypeptide (530 amino acids long) encoded by the mutant c-Src oncogene (SEQ ID NO. 3).

SEQ ID NO. 5 is a 3' mutant allele specific primer containing the complement to the mutant base at the 3' end and a 3-nitropyrrole residue(n) 4 bases upstream of the 3' end.

SEQ ID NO.6 is a wild-type (WT) 3' primer, which is able to amplify both normal wild-type DNA as well as mutant DNA.

SEQ ID NO. 7 is an exemplary sequence of an antisense molecule that is complimentary to the 5' region of the c-Src gene.

5. DETAILED DESCRIPTION OF THE INVENTION

By restriction fragment length polymorphism analysis (RFLP), mutant allele-specific PCR analysis, and direct sequencing, a truncating mutation in Src at codon 531 is identified in 12% of cases of advanced human colon cancer. Other cancers with activated tyrosine kinase are also identified as having SRC 531 mutation (see Example infra). The mutation is found as being activating, transforming, tumorigenic, and metastasis promoting. These observations provide, for the first time, the genetic evidence that the activating SRC mutation plays a significant role in the malignant progression of cancer.

To assess the potential for SRC mutations in cancer, polymerase chain reaction (PCR) primers are constructed to specifically amplify exon 12 of human Src sequences from genomic DNA.

Surprisingly, automated sequencing of PCR products reveals a heterozygous C-T transition mutation in codon 531. This is further confirmed by manual sequencing (FIG. 1a) in several human colon cancer specimens with known elevated c-Src protein kinase activity. Because the mutation in codon 531 generates a ScaI restriction site, a rapid screen for the SRC 531 mutation is developed using a ScaI-based restriction fragment length polymorphism (RFLP) assay.

Figure 1B:
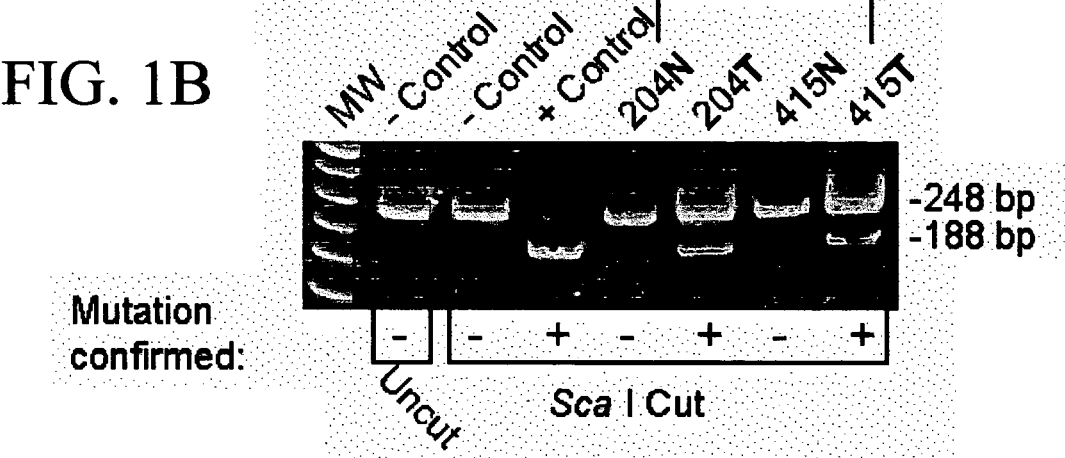
Figure 1C:
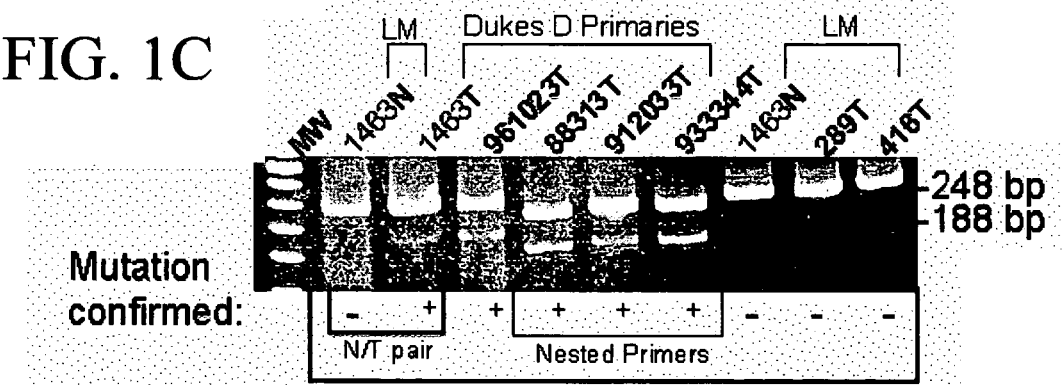
Figure 1D:
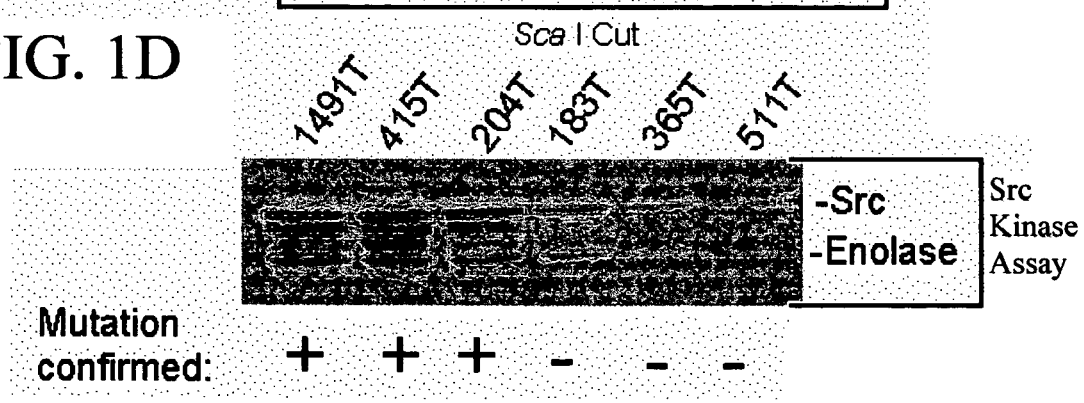

FIG. 1b, c discloses that, 124 early stage (TanyNanyM0) tumors without distant metastases and late stage (TanyNanyM1) colon cancer specimens with distant metastases (including direct analysis of liver-metastatic lesions) are screened for point mutation of codon 531. Nine positive samples are confirmed by direct sequencing analysis. All tumors (100%) harboring the mutation are of late stage (M1) and, of those available for testing, all demonstrate high levels of c-Src protein kinase activity (FIG. 1d). None of the tumors harboring the mutation demonstrate microsatellite instability or any other gross genomic aberration. The SRC 531 mutation results in the production of a stop codon at residue 531, thereby truncating the c-Src protein (SEQ ID NO. 2) directly C-terminal to the regulatory Tyr 530, producing the mutated c-Src 531 polypeptide of SEQ ID NO. 4. Although 46 primary, early stage, human colon cancer specimens are screened with this assay, no SRC 531 imutation is detected in any of these tumors. No DNA derived from normal adjacent matched tissue samples or in normal genomic DNA samples from patients with tumors harbor the SRC 531 mutation.

To confirm the presence of the SRC 531 mutation, an allele-specific oligonucleotide PCR based assay (Guo, Z., Liu, Q. & Smith, L. M. Enhanced discrimination of single nucleotide polymorphisms by artificial mismatch hybridization. Nat. Biotechnol. 15, 331–335 (1997)) is also performed by amplifying the mutant allele using one base mismatch PCR primers containing one 3' end and a 3-nitropyrrole residue (FIG. 2). PCR products are created with a 3' mutant allele specific primer (5' TAGAGGTTCTCCCCZGGCTA 3') (SEQ ID NO.5) containing the complement to the mutant base at the 3' end and a 3-nitropyrrole residue (Z) 4 bases upstream of the 3' end. The mutant allele specific primer is capable of amplifying mutant DNA derived from frozen or paraffin-embedded tumors, but is unable to produce a product from normal DNA. At the same time, a wild-type (WT) 3' primer (5' TAGAGGTTCTCCCCGGCTG 3') (SEQ ID NO. 6) is able to amplify both normal wild-type DNA as well as mutant DNA. These experiments show that the mutant allele is amplified in tumor samples, whereas the wild-type allele is not amplified in normal adjacent tissues. Moreover, the SRC 531 mutation is clonal in origin. When careful tumor microdissection is performed in attempt to increase the relative percentage of tumor cells in any given sample, the ratio of the T:C alleles increase proportionately.

Figures 3A, 3B, 3C, 3D:
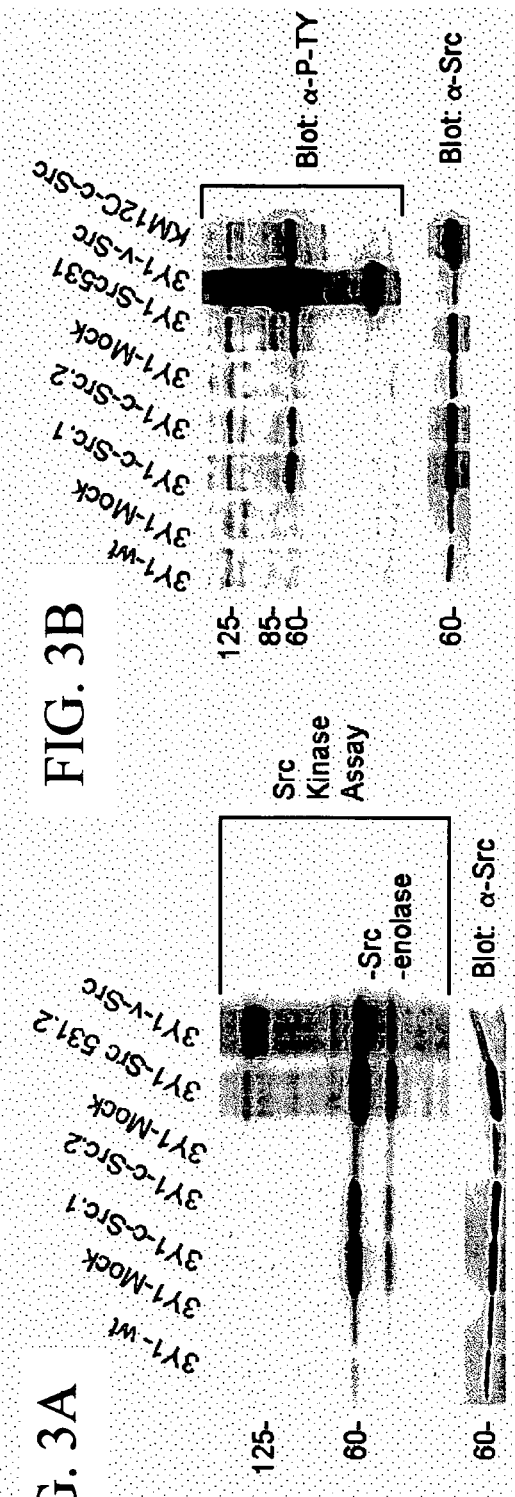

To test the hypothesis that SRC 531 is a transforming mutation, the SRC 531 mutant cDNA is expressed from a mammalian vector with the CMV promoter into rat 3Y1 fibroblasts and NIH 3T3 fibroblasts. To ensure that observed biologic effects are attributable to the SRC 531 mutation, this construct is derived by recombining exon 12 containing a single mutation (SRC 531) derived from a human colon cancer with exons 1–11 derived from normal human c-Src cDNA. Src Western blots show that the 60 kD SRC 531 mutant protein level is elevated approximately 5–10 fold over mock controls, but levels of expression are equivalent to cells transfected with normal human c-Src vector (FIG. 3a). The kinase activity of cells overexpressing SRC 531 is approximately 6 fold greater than that of cells overexpressing similar amounts of c-Src, but less than that of v-Src. By comparison, the kinase activity of cells overexpressing v-Src is more than 12 fold greater than cells overexpressing c-Src. Quantitation of Src protein kinase activity is based on phosphorylation of the exogenous substrate, enolase, and is normalized to Src protein expression levels shown in the Src Western blot. Note that v-Src transfectants generally produce less Src protein than other transfectants. Quantitation of Src autokinase levels found c-Src overexpressing clones with 3–5 fold greater activity than mock or wild type cells, whereas the overexpressing SRC 531 clone and the v-Src clone produced autokinase levels that are increased 2–4 fold further.

The levels of total protein tyrosine phosphorylation increase with the degree of expression and mutational activation: mock<c-Src<SRC 531<v-Src (FIG. 3b,c). Various clones expressing SRC 531 shown in panel c show significant increases in Src phosphotyrosine levels and phosphorylation of new substrates when compared with mock transfected controls or one representative clone overexpressing wild-type c-Src. Quantitation of Src phosphotyrosine levels when normalized to protein levels of Src found the c-Src overexpressing clone with 2.2 fold greater levels than mock transfected cells whereas SRC 531 overexpressing clones had 3.9–6.6 fold greater levels than mock transfected cells. As expected, v-Src transfectants had phosphotyrosine levels that are significantly greater (18 fold) than mock transfected cells. Consistent with these findings, in vitro levels of autokinase activity and levels of activity towards the exogenous substrate enolase are significantly elevated in the mutant forms of Src (FIG. 3a).

To address the mechanism of activation of SRC 531, cyanogen bromide cleavage mapping is performed on orthophosphate-labeled Src from fibroblasts stable transfected with vectors encoding c-Src (wild type) (SEQ ID NO. 2), SRC 531 (SEQ ID NO. 4), or v-Src. These experiments demonstrate that the autophosphorylation site, Tyr 419 present in the 10 kD band, is highly phosphorylated in both the mutant SRC 531 and in the v-Src transfectants, consistent with elevations in Src autokinase activity. In contrast, the cells transfected with wild-type c-Src (SEQ ID NO. 1) show only significant phosphorylation of the 4–6 kD fragment known to contain the C-terminal Tyr 530 (FIG. 3d). Tyr 530 in SRC 531 is shifted to 3.5 kD, consistent with a truncated peptide 6 amino acids shorter and is phosphorylated. These results indicate that in the SRC 531 mutant (SEQ ID NO. 4), Tyr 530 phosphorylation is present but not capable of functioning in a negative regulatory role as postulated for wild type c-Src (SEQ ID NO. 2), in the prior art.

The SRC 531 interfering compounds of the present invention can occur as racemates, racemic mixtures, and as individual enantiomers or diastereoisomers, with all isomeric forms being included in the present invention as well as mixtures thereof.

Pharmaceutically acceptable salts of the compounds of the invention where a basic or acidic group is present in the structure, are also included within the scope of this invention. When an acidic substituent is present, such as —COOH, there can be formed the ammonium, sodium, potassium, calcium salt, and the like, for use as the dosage form. When a basic group is present, such as amino or a basic heteroaryl radical, such as pyridyl, an acidic salt, such as hydrochloride, hydrobromide, acetate, maleate, pamoate, methanesulfonate, p-toluenesulfonate, and the like, can be used as the dosage form.

Also, in the case of the —COOH being present, pharmaceutically acceptable esters can be employed, e.g., methyl, tert-butyl, pivaloyloxymethyl, and the like, and those esters known in the art for modifying solubility or hydrolysis characteristics for use as sustained release or prodrug formulations.

In addition, some of the compounds of the instant invention can form solvates with water or common organic solvents. Such solvates are encompassed within the scope of the invention.

The term "therapeutically effective amount" shall mean that amount of drug or pharmaceutical agent that will elicit the biological or medical response of a tissue, system, animal, or human that is being sought by a researcher, veterinarian, medical doctor or other clinician. Generally, a daily dose of about 0.5 mg/Kg to 100 mg/Kg body weight in divided doses is suggested. Such dosage has to be individualized by the clinician.

The present invention also has the objective of providing suitable topical, oral, and parenteral pharmaceutical formulations for use in the novel methods of treatment of the present invention. The compounds of the present invention can be administered orally as tablets, aqueous or oily suspensions, lozenges, troches, powders, granules, emulsions, capsules, syrups or elixirs. The composition for oral use can contain one or more agents selected from the group of sweetening agents, flavoring agents, coloring agents and preserving agents in order to produce pharmaceutically elegant and palatable preparations. The tablets contain the acting ingredient in admixture with non-toxic pharmaceutically acceptable excipients which are suitable for the manufacture of tablets. These excipients can be, for example, inert diluents, such as calcium carbonate, lactose, calcium phosphate or sodium phosphate; granulating and disintegrating agents, such as corn starch or alginic acid; binding agents, such as starch, gelatin or acacia; and lubricating agents, such as magnesium stearate, stearic acid or talc. These tablets can be uncoated or coated by known techniques to delay disintegration and absorption in the gastrointestinal tract and thereby provide a sustained action over a longer period. For example, a time delay material such as glyceryl monostearate or glyceryl distearate can be employed.

Formulations for oral use can be in the form of hard gelatin capsules wherein the active ingredient is mixed with an inert solid diluent, for example, calcium carbonate, calcium phosphate or kaolin. They can also be in the form of soft gelatin capsules wherein the active ingredient is mixed with water or an oil medium, such as peanut oil, liquid paraffin or olive oil.

Aqueous suspensions normally contain the active materials in admixture with excipients suitable for the manufacture of aqueous suspension. Such expicients can be: suspending agent such as sodium carboxymethyl cellulose, methyl cellulose, hydroxypropylmethylcellulose, sodium alginate, polyvinylpyrrolidone, gum tragacanth and gum acacia; dispersing or wetting agents which can be naturally occurring phosphatide such as lecithin; a condensation product of an alkylene oxide with a fatty acid, for example, polyoxyethylene stearate; a condensation product of ethylene oxide with a long chain aliphatic alcohol, for example, heptadecaethylenoxycetanol; a condensation product of ethylene oxide with a partial ester derived from a fatty acid and hexitol such as polyoxyethylene sorbitol monooleate, or a condensation product of ethylene oxide with a partial ester derived from fatty acids and hexitol anhydrides, for example polyoxyethylene sorbitan monooleate.

The pharmaceutical compositions can be in the form of a sterile injectable aqueous or oleagenous suspension. This suspension can be formulated according to known methods using those suitable dispersing or wetting agents and suspending agents which have been mentioned above. The sterile injectable preparation can also comprise a sterile injectable solution or suspension in a non-toxic parenterally-acceptable diluent or solvent, for example, as a solution in 1,3-butanediol. Among the acceptable vehicles and solvents that can be employed are water, Ringer's solution, and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid find use in the preparation of injectables.

Compounds of the invention can also be administered in the form of suppositories for rectal administration of the drug. These compositions can be prepared by mixing the drug with a suitable non-irritating excipient which is solid at ordinary temperature but liquid at the rectal temperature and will therefore melt in the rectum to release the drug. Such materials are cocoa butter and polyethylene glycols.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Antisense oligonucleotides according to the invention are perfectly suitable for the inhibition of mutant c-Src expression. In the context of this invention, the term "oligonucleotide" refers to an oligomer or polymer of ribonucleic acid (RNA) or deoxyribonucleic acid (DNA) or mimetics thereof. Thus, they represent preparations for inhibiting the over-expressed c-Src in well-calculated fashion. This offers new possibilities of being able to treat by means of gene therapy various diseases linked with the anomalous tyrosine kinase biosynthesis, particularly tumor diseases. The antisense compounds in accordance with this invention preferably comprise from about 8 to about 120 nucleobases. Particularly preferred are antisense oligonucleotides comprising from about 8 to about 30 nucleobases (i.e. from about 8 to about 30 linked nucleosides). As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn the respective ends of this linear polymeric structure can be further joined to form a circular structure, however, open linear structures are generally preferred. Within the oligonucleotide structure, the phosphate groups are commonly referred to as forming the internucleoside backbone of the oligonucleotide. The normal linkage or backbone of RNA and DNA is a 3' to 5' phosphodiester linkage.

Specific examples of preferred antisense compounds useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Preferred modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'–5' linkages, 2'–5' linked analogs of these, and those having inverted polarity wherein the adjacent pairs of nucleoside units are linked 3'–5' to 5'–3' or 2'–5' to 5'–2'. Various salts, mixed salts and free acid forms are also included.

Representative U.S. patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, each of which is herein incorporated by reference.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative U.S. patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

In other preferred oligonucleotide mimetics, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative U.S. patents that teach the preparation of PNA compounds include, but are not limited to, U.S. Pat. Nos. 5,539,082; 5,714,331; and 5,719,262, each of which is herein incorporated by reference. Most preferred embodiments of the invention are oligonucleotides with phosphorothioate backbones and oligonucleosides with heteroatom backbones. Also preferred are oligonucleotides having morpholino backbone structures of the above-referenced U.S. Pat. No. 5,034,506.

Modified oligonucleotides can also contain one or more substituted sugar moieties as described in U.S. Pat. No. 5,945,290 and the content of which is herein incorporated by reference.

Oligonucleotides can also have sugar mimetics such as cyclobutyl moieties in place of the pentofuranosyl sugar. Representative U.S. patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,0531 5,639,873; 5,646,265; 5,658,873; 5,670,633; and 5,700,920, and each of which is herein incorporated by reference. Oligonucleotides can also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine.

Representative U.S. patents that teach the preparation of certain of the above noted modified nucleobases as well as other modified nucleobases include, but are not limited to, the above noted U.S. Pat. No.3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,750,692; and 5,681,941, each of which is herein incorporated by reference.

Another modification of the oligonucleotides of the invention involves chemically linking to the oligonucleotide one or more moieties or conjugates which enhance the activity, cellular distribution or cellular uptake of the oligonucleotide. Such moieties include but are not limited to lipid moieties such as a cholesterol moiety, a thioether, e.g., hexyl-S-tritylthiol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxycholesterol moiety. Representative U.S. patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, each of which is herein incorporated by reference.

It is not necessary for all positions in a given compound to be uniformly modified, and in fact more than one of the aforementioned modifications can be incorporated in a single compound or even at a single nucleoside within an oligonucleotide. The present invention also includes antisense compounds which are chimeric compounds. "Chimeric" antisense compounds or "chimeras," in the context of this invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide can serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art.

Chimeric antisense compounds of the invention can be formed as composite structures of two or more oligonucleotides, modified oligonucleotides, oligonucleosides and/or oligonucleotide mimetics as described above. Such compounds have also been referred to in the art as hybrids or gapmers. Representative U.S. patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, each of which is herein incorporated by reference.

The antisense compounds used in accordance with this invention can be conveniently and routinely made through the well-known technique of solid phase synthesis. Equipment for such synthesis is sold by several vendors including, for example, Applied Biosystems (Foster City, Calif.). Any other means for such synthesis known in the art can additionally or alternatively be employed. It is well known to use similar techniques to prepare oligonucleotides such as the phosphorothioates and alkylated derivatives.

The antisense compounds of the invention are synthesized in vitro and do not include antisense compositions of biological origin, or genetic vector constructs designed to direct the in vivo synthesis of antisense molecules. The compounds of the invention can also be admixed, encapsulated, conjugated or otherwise associated with other molecules, molecule structures or mixtures of compounds, as for example, liposomes, receptor targeted molecules, oral, rectal, topical or other formulations, for assisting in uptake, distribution and/or absorption. Representative U.S. patents that teach the preparation of such uptake, distribution and/or absorption assisting formulations include, but are not limited to, U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

The antisense compounds of the invention encompass any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to prodrugs and pharmaceutically acceptable salts of the compounds of the invention, pharmaceutically acceptable salts of such prodrugs, and other bioequivalents.

The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention are prepared as SATE [(S-acetyl-2-thioethyl) phosphate] derivatives according to the methods disclosed in WO 93/24510 to Gosselin et al., or in WO 94/26764 to Imbach et al.

The term "pharmaceutically acceptable salts" refers to physiologically and pharmaceutically acceptable salts of the compounds of the invention: i.e., salts that retain the desired biological activity of the parent compound and do not impart undesired toxicological effects thereto. Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine. The base addition salts of said acidic compounds are prepared by contacting the free acid form with a sufficient amount of the desired base to produce the salt in the conventional manner. The free acid form can be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention. As used herein, a "pharmaceutical addition salt" includes a pharmaceutically acceptable salt of an acid from one of the components of the compositions of the invention. These include organic or inorganic acid salts of the amines. Preferred acid salts are the hydrochlorides, acetates, salicylates, nitrates and phosphates. Other suitable pharmaceutically acceptable salts are well known to those skilled in the art and include basic salts of a variety of inorganic and organic acids, such as, for example, with inorganic acids, such as for example hydrochloric acid, hydrobromic acid, sulfuric acid or phosphoric acid; with organic carboxylic, sulfonic, sulfo or phospho acids or N-substituted sulfamic acids, for example acetic acid, propionic acid, glycolic acid, succinic acid, maleic acid, hydroxymaleic acid, methylmaleic acid, fumaric acid, malic acid, tartaric acid, lactic acid, oxalic acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid; and with amino acids, such as the 20 alpha-amino acids involved in the synthesis of proteins in nature, for example glutamic acid or aspartic acid, and also with phenylacetic acid, methanesulfonic acid, ethanesulfonic acid, 2-hydroxyethanesulfonic acid, ethane-1,2-disulfonic acid, benzenesulfonic acid, 4-methylbenzenesulfonic acid, naphthalene-2-sulfonic acid, naphthalene-1,5-disulfonic acid, 2- or 3-phosphoglycerate, glucose-6-phosphate, N-cyclohexylsulfamic acid (with the formation of cyclamates), or with other acid organic compounds, such as ascorbic acid. Pharmaceutically acceptable salts of compounds can also be prepared with a pharmaceutically acceptable cation. Suitable pharmaceutically acceptable cations are well known to those skilled in the art and include alkaline, alkaline earth, ammonium and quaternary ammonium cations. Carbonates or hydrogen carbonates are also possible.

For oligonucleotides, preferred examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine. The antisense compounds of the present invention can be utilized for diagnostics, therapeutics, prophylaxis and as research reagents and kits. For therapeutics, an animal, preferably a human, suspected of having a disease or disorder which can be treated by modulating the expression of c-Src is treated by administering antisense compounds in accordance with this invention. The compounds of the invention can be utilized in pharmaceutical compositions by adding an effective amount of an antisense compound to a suitable pharmaceutically acceptable diluent or carrier. Use of the antisense compounds and methods of the invention can also be useful prophylactically, e.g., to prevent or delay infection, inflammation or tumor formation, for example.

The antisense compounds of the invention are useful for research and diagnostics, because these compounds hybridize to nucleic acids encoding c-Src, enabling sandwich and other assays to easily be constructed to exploit this fact. Hybridization of the antisense oligonucleotides of the invention with a nucleic acid encoding c-Src can be detected by means known in the art. Such means can include conjugation of an enzyme to the oligonucleotide, radiolabelling of the oligonucleotide or any other suitable detection means. Kits using such detection means for detecting the level of c-Src in a sample can also be prepared.

The present invention also includes pharmaceutical compositions and formulations which include the antisense compounds of the invention. The pharmaceutical compositions of the present invention can be administered in a number of ways depending upon whether local or systemic treatment is desired and upon the area to be treated. Administration can be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Oligonucleotides with at least one 2'-O-methoxyethyl modification are believed to be particularly useful for oral administration.

Pharmaceutical compositions and formulations for topical administration can include transdermal patches, ointments, lotions, creams, gels, drops, suppositories, sprays, liquids and powders. Conventional pharmaceutical carriers, aqueous, powder or oily bases, thickeners and the like can be necessary or desirable. Coated condoms, gloves and the like can also be useful.

Compositions and formulations for oral administration include powders or granules, suspensions or solutions in water or non-aqueous media, capsules, sachets or tablets. Thickeners, flavoring agents, diluents, emulsifiers, dispersing aids or binders can be desirable.

Compositions and formulations for parenteral, intrathecal or intraventricular administration can include sterile aqueous solutions which can also contain buffers, diluents and other suitable additives such as, but not limited to, penetration enhancers, carrier compounds and other pharmaceutically acceptable carriers or excipients.

Pharmaceutical compositions and/or formulations comprising the oligonucleotides of the present invention can also include penetration enhancers in order to enhance the alimentary delivery of the oligonucleotides. Penetration enhancers can be classified as belonging to one of five broad categories, i.e., fatty acids, bile salts, chelating agents, surfactants and non-surfactants. One or more penetration enhancers from one or more of these broad categories can be included.

Various fatty acids and their derivatives which act as penetration enhancers include, for example, oleic acid, lauric acid, capric acid, myristic acid, palmitic acid, stearic acid, linoleic acid, linolenic acid, dicaprate, tricaprate, recinleate, monoolein (a.k.a. 1-monooleoyl-rac-glycerol), dilaurin, caprylic acid, arichidonic acid, glyceryl 1-monocaprate, 1-dodecylazacycloheptan-2-one, acylcarnitines, acylcholines, mono- and di-glycerides and physiologically acceptable salts thereof (i.e., oleate, laurate, caprate, myristate, palmitate, stearate, linoleate, etc. Examples of some presently preferred fatty acids are sodium caprate and sodium laurate, used singly or in combination at concentrations of 0.5 to 5%.

Various natural bile salts, and their synthetic derivatives, act as penetration enhancers. Thus, the term "bile salt" includes any of the naturally occurring components of bile as well as any of their synthetic derivatives. A presently preferred bile salt is chenodeoxycholic acid (CDCA) (Sigma Chemical Company, St. Louis, Mo.), generally used at concentrations of 0.5 to 2%.

Complex formulations comprising one or more penetration enhancers can be used. For example, bile salts can be used in combination with fatty acids to make complex formulations. Preferred combinations include CDCA combined with sodium caprate or sodium laurate (generally 0.5 to 5%).

Chelating agents include, but are not limited to, disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines). Chelating agents have the added advantage of also serving as DNase inhibitors.

Surfactants include, for example, sodium lauryl sulfate, polyoxyethylene-9-lauryl ether, polyoxyethylene-20-cetyl etherand perfluorochemical emulsions, such as FC-43.

Non-surfactants include, for example, unsaturated cyclic ureas, 1-alkyl- and 1-alkenylazacyclo-alkanone derivatives and non-steroidal anti-inflammatory agents such as diclofenac sodium, indomethacin and phenylbutazone.

As used herein, "carrier compound" refers to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. For example, the recovery of a partially phosphorothioated oligonucleotide in hepatic tissue is reduced when it is coadministered with polyinosinic acid, dextran sulfate, polycytidic acid or 4-acetamido-4'-isothiocyano-stilbene-2,2'-disulfonic acid.

In contrast to a carrier compound, a "pharmaceutically acceptable carrier" (excipient) is a pharmaceutically acceptable solvent, suspending agent or any other pharmacologically inert vehicle for delivering one or more nucleic acids to an animal. The pharmaceutically acceptable carrier can be liquid or solid and is selected with the planned manner of administration in mind so as to provide for the desired bulk, consistency, etc., when combined with a nucleic acid and the other components of a given pharmaceutical composition. Typical pharmaceutically acceptable carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrates (e.g., starch, sodium starch glycolate, etc.); or wetting agents (e.g., sodium lauryl sulphate, etc.). Sustained release oral delivery systems and/or enteric coatings for orally administered dosage forms are described in U.S. Pat. Nos. 4,704,295; 4,556,552; 4,309,406; and 4,309,404.

The compositions of the present invention can additionally contain other adjunct components conventionally found in pharmaceutical compositions, at their art-established usage levels. Thus, for example, the compositions can contain additional compatible pharmaceutically-active materials such as, e.g., antipruritics, astringents, local anesthetics or anti-inflammatory agents, or can contain additional materials useful in physically formulating various dosage forms of the composition of present invention, such as dyes, flavoring agents, preservatives, antioxidants, opacifiers, thickening agents and stabilizers. However, such materials, when added, should not unduly interfere with the biological activities of the components of the compositions of the invention.

Regardless of the method by which the antisense compounds of the invention are introduced into a patient, colloidal dispersion systems can be used as delivery vehicles to enhance the in vivo stability of the compounds and/or to target the compounds to a particular organ, tissue or cell type. Colloidal dispersion systems include, but are not limited to, macromolecule complexes, nanocapsules, microspheres, beads and lipid-based systems including oil-in-water emulsions, micelles, mixed micelles, liposomes and lipid:oligonucleotide complexes of uncharacterized structure. A preferred colloidal dispersion system is a plurality of liposomes. Liposomes are microscopic spheres having an aqueous core surrounded by one or more outer layer(s) made up of lipids arranged in a bilayer configuration.

Certain embodiments of the invention provide for liposomes and other compositions containing (a) one or more antisense compounds and (b) one or more other chemotherapeutic agents which function by a non-antisense mechanism. Examples of such chemotherapeutic agents include, but are not limited to, anticancer drugs such as daunorubicin, dactinomycin, doxorubicin, bleomycin, mitomycin, nitrogen mustard, chlorambucil, melphalan, cyclophosphamide, 6-mercaptopurine, 6-thioguanine, cytarabine (CA), 5-fluorouracil (5-FU), floxuridine (5-FUdR), methotrexate (MTX), colchicine, vincristine, vinblastine, etoposide, teniposide, cisplatin and diethylstilbestrol (DES). See, generally, The Merck Manual of Diagnosis and Therapy, 15th Ed., Berkow et al., eds., 1987, Rahway, N.J. Anti-inflammatory drugs, including but not limited to nonsteroidal anti-inflammatory drugs and corticosteroids, and antiviral drugs, including but not limited to ribivirin, vidarabine, acyclovir and ganciclovir, can also be combined in compositions of the invention. See, generally, The Merck Manual of Diagnosis and Therapy, 15th Ed., Berkow. et al., eds., 1987, Rahway, N.J., pages 2499–2506. Other non-antisense chemotherapeutic agents are also within the scope of this invention. Two or more combined compounds can be used together or sequentially.

In another related embodiment, compositions of the invention can contain one or more antisense compounds, particularly oligonucleotides, targeted to a first nucleic acid and one or more additional antisense compounds targeted to a second nucleic acid target. Two or more combined compounds can be used together or sequentially.

The formulation of therapeutic compositions and their subsequent administration is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages can vary depending on the relative potency of individual oligonucleotides. Antisense oligonucleotides according to the invention can be given a person as such, individually or in combination. However, they can also be expressed within the person by means of an expression vector containing sequences encoding for them.

Those of skill in treating disorders which are amenable to regulation by antisense constructs can determine the effective amount of a particular antisense construct to be formulated in a pharmaceutical preparation. In general it is contemplated than an effective amount would be from 0.001 mg/kg to 50 mg/kg body weight and more preferably from 0.01 mg/kg to 10 mg/kg body weight. There are numerous methods that have been formulated for inhibiting specific gene expression which have been adopted to some degree and have been defined as antisense nucleic acids, e.g., U.S. Pat. No. 5,856,103. The basic approach is that an antisense oligonucleotide (ASO) analog complimentary to a specific targeted messenger RNA or mRNA sequence is used. The term "antisense" as used herein is a term denoting a novel approach to chemotherapy which is based upon the complementary pairing of ASO nucleic acids with a target nucleic acid. The use of such a compound requires a complementarity of the antisense base sequence to a target zone of an mRNA, so that the antisense ASO will bind to that mRNA target sequence and will bring about selective inhibition of gene expression.

When the method of the present invention is used to enhance the immune response of a subject who has a cancer, hypersensitivity disease, or autoimmune disorder, the method can be used to correct a deficiency or imbalance in the immune system. The method of the present invention can be used to alter the immune response of a subject so as to prompt the suppressor cells to mount an immunological attack on the aberrant T/cells.

When the immune system of a subject is enhanced by challenging the immune system with an antigen responsible for tumorigenesis (SRC 531 mutant), the method of the present invention can be used prophylactically or therapeutically. For example, the method can be used prophylactically when the immune response of a subject is enhanced before the subject is afflicted with a disease. Hence, the immune system response of a subject can be enhanced to increase the vigor of the immune response prior to acquiring the disease.

The method of the present invention can also be used therapeutically such as when a subject has a disease, i.e., colon cancer, so that said cancer is eliminated or spread of metastatic cells is reduced or eliminated. Subjects in need of such an intervention can be vaccinated according to the methods of the present invention in order to alter the immune system response of the subject and achieve a beneficial therapeutic effect.

6. EXAMPLES

6.1 Example

PCR and RFLP Analysis of Tumors

Total RNA is isolated from frozen human tumor specimens expressing various levels of Src kinase activity and subjected to RT-PCR using primers designed to amplify the 600 base pairs (bp) at the 3' end of the cDNA as described in Tanaka, A. et al. DNA sequence encoding the amino-terminal region of the human c-Src protein: implications of sequence divergence among Src-type kinase oncogenes. Mol Cell Biol 7, 1978–1983 (1987) and Tanaka, A. & Fujita, D. J. Expression of a molecularly cloned human c-Src oncogene by using a replication-competent retroviral vector. Mol Cell Biol 6, 3900–3909 (1986). RT-PCR products are cloned and sequenced manually as well as by automated sequencing. Tumors are screened for presence of the SRC 531 mutation by RFLP analysis of PCR products 248 bp in length digested to completion with ScaI restriction enzyme. Other technical variations of above disclosed means of manipulating DNA, preparing primers, and restriction enzyme analysis are well known in the art such as disclosed for example in U.S. Pat. No. 5,783,182

6.2 Example

Soft Agar and Matrigel Invasion Assays v-Src has been shown earlier to induce the production of specific metalloproteinases and to foster the metastatic phenotype. For this reason, SRC 531 transfectants are assessed in vitro for potential to invade matrigel. To determine transformation potential of SRC 531, fibroblasts stably transfected with c-Src (SEQ ID NO. 1), SRC 531 (SEQ ID NO. 3) or v-Src are subjected to soft agar colony formation assays to assess anchorage independent growth (FIG. 4a,b). Equal numbers of 3Y1 cells, either wild type cells or cells transfected with pcc-Src, pcSrc531RI, or a vector carrying v-Src are seeded in 0.5% agar and cells are incubated for 10–14 days until colonies are formed. These experiments demonstrate significant colony formation for only the mutant forms of Src, although very small, slowly growing colonies are occasionally detected in normal human c-Src transfectants. Because these assays examine essentially single clones of transfected cells, focus formation assays are performed to assess the ability of the SRC 531 mutant to transform populations of cells. Again, these experiments demonstrate (FIG. 4c) the capacity for both mutant forms of Src to produce foci, although the v-Src transfectants consistently produce more foci in less time than SRC 531 transfectants. Note that v-Src associated foci are visible within 10 days with 1 µg (micrograms) DNA, whereas SRC 531 associated foci are visible only after 21 days of culture at doses of 10 µg (micrograms) DNA. Furthermore, rapid subcutaneous tumor growth results from tumor cells inoculated into the nude mouse in all clones tested (see Example infra).

For the Matrigel assay, $5 \times 10^4$ cells are seeded into matrigel chambers in 200 ml serum free medium with 800 ml full medium in the well below. The cells are allowed to grow for 48 h, after which the layer of cells in the chamber is carefully scraped off and cells adhering to the membrane beneath the chambers are stained with crystal violet and counted.

Both SRC 531 and v-Src transfectants readily invade matrigel, whereas c-Src transfectants does not (FIG. 4d).

6.3 Example

Src Protein Kinase Activity Assay and Immunoblotting

Tumor lysates are prepared in radioimmunoprecipitation assay (RIPA) buffer (10 mM Tris pH 7.4, 150 mM NaCl, 10% glycerol, 5 mM EDTA, 1% Triton-X 100, 0.5% deoxycholate, 1mM PMSF, 1 mM Na orthovanadate, 10 mg/ml leupeptin, 10 mg/ml apoprotinin), clarified by microcentrifugation for 15 min at 4° C., immunoprecipitated with anti-Src Ab (MAB 327), and then washed three times with RIPA buffer and three times in Tris buffer (40 mM Tris pH 7.4). The samples are then resuspended in 30 ml of kinase reaction buffer (20 mM Tris pH 7.4, 5 mM magnesium chloride, 10 mm sodium orthovanadate) containing 20 µCi (microcuries) [$^{32}$P]ATP/sample and enolase (1 mg/sample) as exogenous substrate. The obtained samples are incubated for 15 min at room temperature, resuspended in electrophoresis sample buffer, boiled 5 min and loaded onto a SDS-10% polyacrylamide gel.

Immunoblotting or Western Blot is performed as previously described (Mao, W. et al. Activation of c-Src by receptor tyrosine kinases in human colon cancer cells with high metastatic potential. *Oncogene* 15, 3083–3090 (1997)). At the end of the incubation period, the filters are washed and incubated with the appropriate horseradish peroxidase-conjugated secondary antibodies for 1 hour at room temperature. The filters are then washed and exposed with the enhanced chemiluminescence detection system (Amersham).

6.4 Example

CNBr Cleavage Studies

Cells transfected with pcc-Src, pcSrc531RI, and v-Src are labeled with 3.3 mCi each of inorganic $^{32}$P for 4 hours. Cell lysates are immunoprecipitated with α-Src (alpha-Src) monoclonal antibody and washed immunoprecipitates are subjected to SDS-PAGE, the gel dried and exposed to X-ray film. The visible Src bands are excised and incubated with 50 mg/ml CNBr in 70% formic acid for 1 h at room temperature as described (Jove, R., Hanafusa, T., Hamaguchi, M. & Hanafusa, H. In vivo phosphorylation states and kinase activities of transforming p60c-Src mutants. *Oncogene* Res. 5, 49–60 (1989); Jove, R., Kombluth, S. & Hanafusa, H. Enzymatically inactive p60c-Src mutant with altered ATP-binding site is fully phosphorylated in its carboxy-terminal regulatory region. Cell 50, 937–943 (1987)).

The bands are washed in water, dried, and placed in the wells of a 16.5% polyacrylamide gel containing 10% glycerol.

6.5 Example

Cloning of SRC 531 and Transfection of Mammalian Cells

The mutant SRC 531 cDNA is cloned into the expression vector pcDNA3.1 (Invitrogen) creating pcSrc531RI. Normal human SRC cDNA is also inserted into pcDNA3.1-, creating pcc-Src. 3Y1 rat fibroblast cells are transfected with pcSrc531RI, pcc-Src, and a v-Src vector; transfectants are selected with G418. Those colonies overexpressing the Src protein are expanded and used for further tests.

6.6 Example

Mouse Studies

The in vivo potential of transfected cells to metastasize to the lungs following intravenous injection is assessed. Fifteen Balb/c nude mice are injected through the tail vein with $5\times10^5$ cells in PBS. Five mice are injected with each of the 3Y1 cell lines transfected with pcc-Src, pcSrc531RI, or v-Src. Each mouse is also injected with the same cells subcutaneously to monitor tumor growth. Tumors are measured every two days, and mice are sacrificed as they become ill. The lungs are removed to observe metastatic lesions, and are subjected to immunocytochemical studies to determine the levels of Src protein.

v-Src and SRC 531 transfectants both produce extensive experimental lung metastases, while c-Src and mock controls produce none (FIG. 4e). The SRC 531 transfectants cause 100% mortality after 27 days, whereas v-Src transfectants expressing a more active form of Src cause earlier mortality by day 12. In contrast, c-Src transfectants produce no lung metastases and all mice survive beyond 45 days.

6.7 Example

Findings of SRC 531 Mutant in Other Types of Tumors

Mutated pp60c-Src activity is elevated in all five hairy cell leukemia specimens and in a number of the large cell and immunoblastic lymphomas; neoplasms representing later stages in B-cell development. pp60c-Src activity is low in neoplastic cells which correspond to early and intermediate stages in B-cell development (acute and chronic lymphatic leukemia, lymphoblastic lymphoma, small lymphocytic lymphoma).

Mutated pp60c-Src activity is elevated in tested specimens from other varieties of advanced tumors such as fibrosarcoma, myxosarcoma, liposarcoma, chondrosarcoma, osteogenic sarcoma, chordoma, angiosarcoma, Kaposi's sarcoma, endotheliosarcoma, lymphangiosarcoma, lymphangioendotheliosarcoma, synovioma, mesothelioma, Ewing's tumor, leiomyosarcoma, rhabdomyosarcoma, rhabdosarcoma, colorectal carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, neuroblastoma, retinoblastoma, and myeloma albeit at lesser frequency.

6.8 Example

Tumors with Aberrant Src Protein Elicit T Cells Specific Against Mutant Src and Vaccine Against Src-caused Cancer and Metastases The following experiments show that aberrant pp60 protein produced by tumor cells elicits T cells, which proliferate specifically in response to the altered region of the pp60 protein. B6 mice are immunized twice at two-week intervals with cells transfected with pcSrc531RI. Normal human SRC cDNA is also inserted into pcDNA3.1-. 3Y1 rat fibroblast cells are transfected with pcSrc531RI or normal pcc-Src. Spleen cells from mice immunized with FBL transfected with the T24 oncogene proliferate in response to the mutant Src, whereas spleen cells from mice immunized with fibroblasts transfected with normal c-Src do not respond.

The finding that tumors which express aberrant Src-pp60 in vivo can elicit src-specific T cells strongly implies that pp60 is available to antigen-presenting cells (APC) for processing and presentation to class II-restricted T cells in vivo. Presentation of the activated pp60 in proximity to tumor cells elicits class II-restricted T cells which can provide substantial therapeutic effects in vivo against tumors even if the latter do not express class II MHC molecules and cannot be directly recognized. The tumor, which expresses a transfected mutant Src oncogene and is tumorigenic in BALB/c mice, is used in therapy. Small doses of tumor cells ($3\times10^6$), injected i.v., kill animals within 4 weeks. A T cell line specific for the altered region of pp60 is tested for the ability to protect BALB/c mice against challenge with tumor cells. In repeated experiments, mice injected with tumor alone all died by day 27, whereas mice injected concurrently with tumor cells plus Src specific T cells ($2\times10^7$ cells) all survived without evidence of tumor for greater than 8 weeks of observation. Therefore, Src-specific class II-restricted T cells mediate anti-tumor protection in vivo.

From a patient with a late stage metastatic colon carcinoma a biopsy of tumor cells is surgically excised from a liver. Obtained tissue is minced, cells enzymatically isolated and either frozen in liquid nitrogen or cultured in vitro under typical conditions. Alternatively, normal host cells are transfected with a vector disclosed in Example 6.5 so that cells overexpressing the Src protein are expanded and used for further manipulations. After obtaining a suitable number of cells, they are lysed and mixed with antigen-presenting dendritic cells of a patient in need of a vaccine. Dendritic cells are further incubated for 1–3 days with appropriate stimuli such as IL-2 or other growth factor. Then the mixture (about $5\times10^6$ cells per injection) is subcutaneously or intravenously administered back to the patient. The preparation is used either with or without additional immunoadjuvants. Four injections are administered in two weeks intervals followed by three injections once a month. If necessary injections are continued in two months intervals. This so-called "vaccine therapy" approach primes the patient's immune system against his own tumor cells and helps to eliminate tumor cells. The survival of six out of eleven treated patients for over 3 years is statistically better in comparison with survival of less than 2% for patients who are not vaccinated with the vaccine based on use of SRC 531 mutation.

Other means of preparing cancer vaccine and using vaccine are known in the art, such as for example disclosed in U.S. Pat. Nos. 5,156,841, 5,039,522, 5,635,188, 5,646,009, 5,338,674, 5,158,769 and are equally suitable as long as they are adaptable for a practical use within the scope of the present invention.

6.9 Example

Screening for Inhibitory Compounds Using Mutant pp60

A library of peptides to be tested as antagonists of pp60 c-Src mutant tyrosine kinase are synthesized according to the procedure disclosed in U.S. Pat. No. 5,532,167 to Cantley, which is incorporated herein by way of reference. Accordingly a peptide Ala-Glu-Glu-Glu-Ile-Tyr-Gly-Glu-Phe-Glu-Ala-Lys-Lys-Lys-Lys is synthesized as an optimal substrate/antagonist for mutant Src tyrosine kinase. The kinetic studies are carried out as follows. Purified mutant kinase is immobilized on protein A beads and kinase reaction is performed in 20 µl of 50 mM Tris pH 7.0 buffer containing 50 mM NaCl, 10 mM $MgCl_2$, 10 µM ATP 5 µCi [gamma-$^{32}$P]-ATP (3000 mCi/mmol, NEN) and various dilutions of the peptide. For the experiment measuring the competitive inhibition of c-Src activity by the Src motif-containing peptide, 1 µM (final concentration) acid treated enolase (trans-phosphorylation) is included. After 2.5 minutes incubation, the supernatants are spotted on phosphocellulose paper, washed four times with 75 mM phosphoric acid, and radioactivity counted in a scintillation counter. For phosphorylation of enolase, the reaction is stopped by adding SDS loading buffer and the proteins are resolved on 10% SDS-PAGE gels. The Km and Vmax are calculated using a standard computer software. The peptide is a good substrate for pp60c-Src, with Km of 2 µM and Vmax of 0.9 µM/mg/min. The Src-substrate peptide is also an excellent competitive inhibitor of enolase phosphorylation by pp60c-Src ($K_{50\%}$=5 µM).

In addition to peptides as antagonists of mutant pp60Src various other compounds are identified based on the assay disclosed above. These include but are not limited to the antisense molecule, which is complimentary to the 5' region of c-Src gene and blocks transcription via triplex formation. An exemplary sequence of the antisense molecule is as follows:

PBS (1 mM stock) and sterile filtered with Millipore 0.2 micrometer disks. The sequence used for antisense inhibitory studies on SRC gene is a 27 base region of the corresponding mRNA spanning the AUG translation initiation codon. While the present invention is not limited to such sequences, antisense oligonucleotides directed against the initiation codon region of the mRNA are one type of antisense molecule believed to effectively inhibit translation of the resulting gene product. Other effective antisense molecules can be specifically targeted against the opposite end of the mRNA.

To selectively interfere with the expression of mutated SRC gene (SEQ ID NO.3), 5 mice are injected once with 5 µg/g weight of antisense, phosphorothioated oligodeoxynucleotide prepared as above and which is complementary to the initiator AUG domain in SRC mRNA or with PBS for controls. Three weeks following the injection, liver biopsies are prepared from all of these mice. Each biopsy is frozen and then sliced into this slices and hybridized with isotope labeled SRC nucleic probes. Following 3 days of exposure to emulsion autoradiography, slides are developed to create silver grains over cells containing SRC mRNAs. Labeling and number of positive cells is decreased in liver specimens of mice treated with antisense phosphorothioated oligodeoxynucleotide demonstrating that antisense interfered with mutated SRC 531 expression. In contrast, in control mice, SRCmRNA levels per cell increased by about 20-fold. The decrease of mutated SRC 531 expression is also confirmed by Western Blot studies using antibodies obtained by methods disclosed in Example 6.10.

The methods of selecting, making, administering, and testing appropriate doses of an antisense molecule along with suitable modifications, adjuvants and molecules are well known in the art and can be found for example in U.S. Pat. Nos. 5,734,039, 5,583,032, 5,756,476, 5,856,103, and 5,677,289 which are incorporated herein by way of reference. In addition to classical antisense molecule targeting AUG sequence one skilled in the art will know to use other suitable approaches such as a non-coding sense sequence, ribosomal frameshifting, and a ribozyme sequence. The details for such approaches can be found for example, in U.S. Pat. Nos. 5,843,723, 5,759,829, 5,707,866, and 5,712,

```
  1 GCCCCGCAGG TGCCTACTGC CTCTCAGTGT CTGACTTCGA CAACGCCAAG GGCCTCAACG

61 TGAAGCACTA CAAGATCCGC AAGCTGGACA GCGGCGGCTT CTACATCACC TCCCGCACCC

121 AGTTCAACAG CCTGCAGCAG CTGGTGGCCT ACTACTCCAG TGAG (SEQ ID NO: 7)
```

This example is not limiting and one skilled in the art can select shorter oligonucleotide according to established procedures. For example, a series of methoxyethylamine 3' end-cap oligodeoxynucleotides are prepared on a Biosearch 8750 DNA synthesizer, using standard H-phosphonate chemistry on controlled pore glass. The 15 or 18-base oligodeoxynucleotides are purified via DMT-on purification on a semi-prep Dynamax C-4 300A column. A secondary DMT-off purification is then performed on the same column. The oligomers are then desalted over a Pharmacia NAP-25 column, converted to the sodium form via Biorad AC 50W-X8 (Na+) 200–400 mesh polyprep column, and then passed over another NAP-25 column. The antisense oligos and their controls, which contained the same bases but in scrambled sequence, are in a similar manner. Lyophilized oligomers used in the following experiments are dissolved in 384 as incorporated herein by way of reference. Without limiting to above anti-sense approaches it is clear that other means are equally suitable such as compositions and methods for the treatment of SRC 531 transformed malignant cells by antisense nucleic acid molecules that can cause the apoptosis of said cells such as disclosed in U.S. Pat. No. 5,935,937, which is incorporated herein by way of reference.

Furthermore, equally suitable antagonists such as tyrphostin, pyrozolopyrimidine and their derivatives and salts are found as useful pharmaceutical compounds. The inhibitory activity of H-89, K252a, H-7, N-(9-acridinyl)maleimide, staurosporine, herbimycin A, isoflavones like genistein, daidzein, quercetin (as disclosed in U.S. Pat. Nos. 5,919,813 and 5,872,223), quinolymethylen-oxindole (as disclosed in U.S. Pat. No. 5,905,149), angelmicin, 2-iminochromene derivatives (as disclosed in U.S. Pat. No. 5,648,378), 5-aminopyrazoles (as disclosed in U.S. Pat. No. 5,922,741) sesquiterpene lactone (as disclosed in U.S. Pat. No. 5,905,089), various benzylidene-Z-indoline compounds (as disclosed in U.S. Pat. No. 5,880,141), urea- and thiourea-type compounds (as disclosed in U.S. Pat. No. 5,773,459), benzopyran compounds (as disclosed in U.S. Pat. No. 5,763,470), polyhydric phenol compounds (as disclosed in U.S. Pat. No. 5,780,008), resorcyclic acid lactones (as disclosed in U.S. Pat. No. 5,674,892), 4-aminopyrrolo[2,3-d]pyrimidines (as disclosed in U.S. Pat. No. 5,639,757), and miscellaneous other phosphotyrosine phosphatase inhibitors (as disclosed in U.S. Pat. No. 5,877,210) is also tested in the same assay system. It is thus clear that the screening assay using mutant pp60 is extremely useful assay in identifying antagonist compounds targeting this particular form of tyrosine kinase.

The utility of this approach is further confirmed by utilizing a Src-transformed fibroblast assay. In this assay the compounds identified above are used to inhibit the proliferation of fibroblasts. In addition to proliferation inhibition the expression of a mutant gene is also monitored by standard art accepted methods aimed at testing the gene expression.

6.10 Example

Production of Anti-Mutant pp60 Monoclonal and Polyclonal Antibodies

A group of three Balb/c female mice (Charles River Breeding Laboratories, Wilmington, Mass.) are injected with 5 µg/dose of purified truncated C-terminal peptide of pp60c-Src in 100 µl Detox adjuvant (RIBI ImmunoChem Res Inc, Hamilton, Mo.) by intraperitoneal injection on days 0, 3, 7, 10, and 14. On day 17 the animals are sacrificed, their spleens are removed and the lymphocytes fused with the mouse myeloma line 653 using 50% polyethylene glycol 4000 by an established procedure (see U.S. Pat. Nos. 5,939,269, and 5,658,791 as incorporated herein by way of reference). The fused cells are plated into 96-well microtiter plates at a density of $2 \times 10^5$ cells/well followed by HAT selection on day 1 post-fusion. Immobilized hybridoma culture supernatants are then reacted with biotinylated mutant pp60 C-terminal peptide. The wells positive for anti-PC-1 antibodies are expanded for further study. These cultures remain stable when expanded and cell lines are cryopreserved. The parental cultures are isotyped and then assayed for their ability to capture and to specifically recognize mutant pp60.

Alternatively, polyclonal rabbit antisera is raised against purified mutant protein peptides Polyclonal antibodies against the C-terminal peptide are obtained by coupling such peptides to Keyhole Limpet Heamocyanin with 0.05% gluteraldehyde, emulsified in Freunds' complete adjuvant and injected intradermally at several sites. The animals are boosted four and seven weeks later with coupled peptide emulsified in Freunds' incomplete adjuvant and bled ten days after the last injection.

Antibodies prepared according to the above procedures are then used for identifying and/or diagnosing tumor cells that express SRC 531 mutation and/or for therapeutic approaches according to standard procedures known in the art, e.g., U.S. Pat. Nos. 5,601,989, 5,563,247, 5,610,276, and 5,405,941, as incorporated herein by way of reference. These same antibodies are used for monitoring expression of SRC 531, such as disclosed in Example 6.9.

6.11 Example

Transgenic Mice

According to the present invention, transgenic animals of any non-human species, including but not limited to mice, rats, rabbits, guinea pigs, pigs, or non-human primates can be produced using any technique known in the art, including but not limited to microinjection, electroporation, cell gun, cell fusion, or functional equivalents (see U.S. Pat. No. 5,550,316). In preferred embodiments of the invention, transgenic animals are generated according to the method disclosed hereinafter. Briefly, this method entails the following. Transgenic offspring are prepared by microinjecting a recombinant nucleic acid construct into fertilized eggs. For example, and not by way of limitation, fertilized mouse eggs can be collected from recently mated females with vaginal plugs, and then microinjected with construct DNA. Construct DNA, at a concentration of about 0.01–3 µg/ml, is microinjected into the male pronucleus of fertilized eggs, in an amount such that the volume of the pronucleus approximately doubles. The injected eggs are then transferred to female mice which had been mated the night before with vasectomized males. See also U.S. Pat. No. 4,873,191 by Wagner and Hoppe.

DNA clones for microinjection are cleaved with appropriate restriction enzymes, such as Sal1, Not1, etc., and the DNA fragments electrophoresed on 1% agarose gels in TBE buffer (U.S. Pat. No. 5,811,633). The DNA bands are visualized by staining with ethidium bromide, excised, and placed in dialysis bags containing 0.3M sodium acetate at pH 7.0. The DNA is then electroeluted into the dialysis bags, extracted with phenol-chloroform (1:1), and precipitated by two volumes of ethanol. The DNA is redissolved in 1 ml of low salt buffer (0.2M NaCl, 20 mM Tris, pH 7.4, and 1 mM EDTA) and purified on an Elutip-D column. The column is first primed with 3 ml of high salt buffer (1M NaCl, 20 mM Tris, pH 7.4, and 1 mM EDTA) followed by washing with 5 ml of low salt buffer. The DNA solutions are passed through the column for three times to bind DNA to the column matrix. After one wash with 3 ml of low salt buffer, the DNA is eluted with 0.4 ml of high salt buffer and precipitated by two volumes of ethanol. DNA concentrations are measured by absorption at 260 nm in a UV spectrophotometer. For microinjection, DNA concentrations are adjusted to about 3 µg/ml in 5 mM Tris, pH 7.4 and 0.1 mM EDTA. Other methods for purification of DNA for microinjection are also known. The purified inserts form pcSrc531RI plasmids are then microinjected into the pronuclei of fertilized (C57BL/6×CBA)F2 mouse embryos and surviving embryos are transferred into pseudopregnant females according to standard procedures such as disclosed in U.S. Pat. Nos. 5,877,397, 5,907,078, 5,849,993, 5,602,309, 5,387,742, which are incorporated herein by way of reference. SRC531 construct is operably linked to a suitable promoter, e.g., RSV long terminal repeat (LTR), glial fibrillary acidic protein (GFAP), or human beta-globin promoter (GF). Mice that developed from injected embryos are analyzed for the presence of transgene sequences by Southern blot analysis of mutant DNA. Transgene copy number is estimated by band intensity relative to control standards containing known quantities of cloned DNA. At 3 to 8 weeks of age, cells are isolated from these animals and assayed for the presence of transgene encoded SRC 531 mutation. All of the control non-transgenic mice tested negative for expression of SRC 531. Southern blot analysis indicates that many of these mice contain one or more copies of the transgene per somatic and/or germ cell. Some mice with high levels of Src expression developed abnormally, including edemas, head deformities, eye, axial system defects and usually these mice did not survive. Surviving transgenic mice exhibit malignant and/or benign transformation early in their life. Tumors include lymphomas, thymomas, fibrosarcomas, angiosarcomas, hemangiomas, neurofibrosarcomas, etc. These mice are useful as a model for studying SRC 531 mutants in vivo for testing, for example, drugs or SRC 531 antagonists.

Throughout this application, various publications and patents have been referenced. The disclosures in these publications or patents are incorporated herein by reference in order to more fully describe the state of the art.

From the foregoing, it will be evident that, although specific embodiments of the invention have been described herein for purposes of illustration, various modifications may be made without deviating from the spirit and scope of the invention.

We claim:

1. An isolated truncated c-Src polypeptide comprising the amino acid sequence consisting of SEQ ID NO:4.

2. A composition comprising an isolated truncated c-Src polypeptide comprising the amino acid sequence consisting of SEQ ID NO:4; and a pharmaceutically acceptable carrier.

3. A composition comprising an isolated truncated c-Src polypeptide comprsing the amino acid sequence consisting of SEQ ID NO:4; and an adjuvant.

* * * * *

UNITED STATES PATENT AND TRADEMARK OFFICE
CERTIFICATE OF CORRECTION

PATENT NO.         : 7,276,581 B2
APPLICATION NO. : 10/887588
DATED                 : October 2, 2007
INVENTOR(S)       : Timothy J. Yeatman and Rosalyn B. Irby It is certified that error appears in the above-identified patent and that said Letters Patent is hereby corrected as shown below:

Column 5,
Line 47, "lie 441" should read --Ile 441--.

Line 56, "A.D. Phosphorylation oftyrosine" should read

--A.D. Phosphorylation of tyrosine--.

Column 6,
Lines 47-50, "other molecules which specifically bind to c-Src SRC 531 mutant (SEQ ID NO. 3).

Various methods are provided for detecting the presence of SRC 531 mutation in Src oncogene contained in a sample." should read --other molecules which specifically bind to c-Src SRC 531 mutant (SEQ ID NO. 3).

Another preferred embodiment of the invention comprises an expression construct for expressing all or a portion of c-Src SRC 531 mutant (SEQ ID NO. 3). Such a construct comprises a promoter; and an oligonucleotide segment having at least one mutated nucleic acid residue of c-Src mutant and located downstream from the promoter, wherein transcription of the segment is initiated at the promoter. A replicable vector comprising the nucleic acid of mutant c-Src is also provided.

The present invention entails a host cell containing a replicable vector or a recombinant host cell having at least one nucleic acid sequence encoding for SRC 531 (SEQ ID NO. 4) mutant as well as a cell line transformed with SRC 531 mutant Src-oncogene (SEQ ID NO. 3). Also contemplated is a host cell comprising the isolated purified nucleic acid corresponding to SRC 531 mutant Src-oncogene.--

UNITED STATES PATENT AND TRADEMARK OFFICE
CERTIFICATE OF CORRECTION

PATENT NO. : 7,276,581 B2
APPLICATION NO. : 10/887588
DATED : October 2, 2007
INVENTOR(S) : Timothy J. Yeatman and Rosalyn B. Irby It is certified that error appears in the above-identified patent and that said Letters Patent is hereby corrected as shown below:

Column 8,
Line 9, "mutant (fruncated) c-Src 531" should read --mutant (truncated) c-Src 531--.

Line 49, "(TanyNanyMO)" should read --(TanyNanyM0)--.

Column 21,
Line 57, "Equal numbers of3Y1" should read --Equal numbers of 3Y1--.

Column 44,
Line 46-47, "A composition comprising an isolated truncated c-Src polypeptide comprsing" should read --A composition comprising an isolated truncated c-Src polypeptide comprising--.

Signed and Sealed this

Twenty-fourth Day of June, 2008

JON W. DUDAS
*Director of the United States Patent and Trademark Office*